(12) United States Patent
Reynolds et al.

(10) Patent No.: US 8,328,729 B2
(45) Date of Patent: Dec. 11, 2012

(54) ACOUSTIC PLETHYSMOGRAPH FOR MEASURING PULMONARY FUNCTION

(75) Inventors: Jeffrey S. Reynolds, Morgantown, WV (US); David G. Frazer, Fairmont, WV (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 1161 days.

(21) Appl. No.: 12/168,829

(22) Filed: Jul. 7, 2008

(65) Prior Publication Data

US 2009/0012395 A1 Jan. 8, 2009

Related U.S. Application Data

(60) Provisional application No. 60/958,537, filed on Jul. 6, 2007.

(51) Int. Cl.
*A61K 5/091* (2006.01)
(52) U.S. Cl. ........................................................ 600/538
(58) Field of Classification Search ........................ None
See application file for complete search history.

(56) References Cited

U.S. PATENT DOCUMENTS

| | | | |
|---|---|---|---|
| 4,841,982 A | 6/1989 | Nikiforov et al. | |
| 5,379,777 A | 1/1995 | Lomask | |
| 6,113,550 A | 9/2000 | Wilson | |
| 6,287,264 B1 | 9/2001 | Hoffman | |
| 6,626,845 B2 | 9/2003 | Lingo, Jr. et al. | |
| 6,902,532 B2 | 6/2005 | Lomask | |
| 7,094,206 B2 | 8/2006 | Hoffman | |

OTHER PUBLICATIONS

Adler et al., "Unrestrained Plethysmography is an Unreliable Measure of Airway Responsiveness in BALB/c and C57BL/6 mice," *J Appl Physiol* 97:286-292, Mar. 19, 2004.
Buxco Research Systems, "Respiration Measurement in the Whole Body Plethysmograph," Jul. 19, 2005, 17 pages.
DeLorme et al., "Pulmonary Function Assessment by Whole-body Plethysmography in Restrained Versus Unrestrained Mice," *J Pharmacol Toxicol Methods*, 47:1-10, 2002.
Deskins et al., "An Acoustic Plethysmograph to Measure Total Infant Body Volume," *J Biomech Eng*, 107:304-308, 1985.
Deskins et al., "Use of a Resonating Cavity to Measure Body Volume," *J Accoust Soc Am*, 77(2):756-758, 1985.
Drazen et al., "Mouse Models of Airway Responsiveness: Physiological Basis of Observed Outcomes and Analysis of Selected Examples Using These Outcome Indicators," *Annu Rev Physiol*, 61:593-625, 1999.
Drorbaugh et al., "A Barometric Method for Measuring Ventilation in Newborn Infants," *Pediatrics*, 16:81-87, 1955.

(Continued)

*Primary Examiner* — Brian J Gangle
(74) *Attorney, Agent, or Firm* — Klarquist Sparkman, LLP

(57) ABSTRACT

The present disclosure concerns embodiments of an acoustic plethysmograph for measuring pulmonary function of an animal, such as a mouse. The plethysmograph in exemplary embodiments can measure thoracic tidal volume of an unrestrained animal. The plethysmograph in exemplary embodiments acoustically excites the chamber containing the animal and detects changes in the acoustic pressure in the chamber, which correlate to the thoracic tidal volume of the animal. Unlike the conventional whole-body plethysmograph, this acoustic plethysmograph provides a direct measure of thoracic tidal volume. The plethysmograph also can be configured to measure chamber flow (the flow of air into and out of the chamber). Specific airway resistance of the animal can then be determined from the thoracic tidal volume and plethysmograph flow measurements.

23 Claims, 11 Drawing Sheets

OTHER PUBLICATIONS

Enhorning et al., "Whole-body Plethysmography, Does it Measure Tidal Volume in Small Animals?," *Can J Physiol Pharmacol*, 76(10-11):945-951, 1998.

Epstein, et al., "A Theoretical Analysis of the Barometric Method for Measurements of Tidal Volume," *Respir Physiol*, 32:105-120, 1978.

Epstein, et al., "Practical Implementation of the Barometric Method for Measurement of Tidal Volume," *J Appl Physiol*, 49:1107-15, 1980.

Flandre et al., "Effect of Somatic Growth, Strain, and Sex on Double-chamber Plethysmographic Respiratory Function Values in Healthy Mice," *J Appl Physiol*, 94:1129-1136, 2003.

Website, "Unrestrained Whole Body Plethysmograpy and Penh," http://www.buxco.com/cons_wbp.htm, 3 pages (retrieved on Nov. 20, 2006).

Website, "Whole Body Chamber with Tether," http://www.buxco.com/pltower.htm, 2 pages (retrieved on Nov. 24, 2006).

Website, "Unrestrained Plethysmograph with Tower for IV Injection," http://www.emkatech.com/?rub=our_products&rub1=hardware&num=2&numfam=9&numhardware=121, 1 page (retrieved on Nov. 24, 2006).

Website, "Mouse Unrestrained Chamber," http://www.kentscientific.com/Respiration/Mouse%20Unrestrained%20Chamber-2-21-0-1426.aspx, 1 page (retrieved on Nov. 24, 2006).

Website, "Plethysmograph Holders," http://www.toxics.com/holder/holderp.html, 2 pages, (retrieved on Nov. 24, 2006).

Hamelmann et al., "Noninvasive Measurement of Airway Responsiveness in Allergic Mice Using Barometric Plethysmography," *Am J Respir Crit Care Med*, 156:766-775, 1997.

Jacky, J. P., "Barometric Measurement of Tidal Volume: Effects of Pattern and Nasal Temperature," *J Appl Physiol*, 49(2):319-325, 1980.

Jimenez et al., "Pre-Term Infant Volume Measurements by Acoustic Plethysmography," *J Biomed Eng*, 15:91-98, 1993.

Lai-Fook et al., "Airway Resistance Due to Alveolar Gas Compression Measured by Barometric Plethysmography in Mice," *J Appl Physiol*, 98: 2204-2218, 2005.

Website, L. S. Starrett Catalog, "Micrometers," http://catalog.starrett.com/catalog/catalog/groupf.asp?GrpTab=Feature@GroupID=570, 2 pages; and http://catalog.starrett.com/catalog/images/objects/1200/1155.jpg, 1 page (retrieved on Feb. 23, 2007).

Lofgren et al., "Restrained Whole Body Plethysmography for Measure of Strain-specific and Allergen Induced Airway Responsiveness in Conscious Mice," *J Appl Physiol*, 101:1495-1505, 2006.

Lundblad et al., "A Reevaluation of the Validity of Unrestrained Plethysmography in Mice," *J Appl Physiol*, 93:1198-1207, 2002.

Mitzner, et al., "Interpreting Penh in Mice," *J Appl Physiol*, 94(2): 828-832, 2003.

Pennock et al., "A Noninvasive Technique for Measurement of Changes in Specific Airway Resistance," *J Appl Physiol*, 46(2):399-406, 1979.

Reynolds, Jeffrey S., "Unrestrained Acoustic Plethysmograph for Measuring Specific Airway Resistance in Mice," *J. Appl Physiol*, 105(2): 711-717, May 1, 2008.

Reynolds, et al., "Unrestrained Acoustic Plethysmograph for Measuring Tidal Volume in Mice," *Annals of Biomed Engin*, 34(9):1494-1499, Sep. 2006.

Schmid WD, "Temperature Gradients in the Nasal Passage of Some Small Mammals," *Comp Biochem Physiol*, 54A:304-308, 1975.

Schwarze et al., "Barometric Whole Body Plethysmography in Mice," *J Appl Physiol* 98:1955-1957, May 2005.

Scott et al., "Diaphragm Ultrasonography as an Alternative to Whole-Body Plethysmography in Pulmonary Function Testing," *J Ultrasound Med*, 25:225-232, 2006.

Sheng et al., "Body Volume and Fat-Free Mass Determinations by Acoustic Plethysmography," *Pediatr Res*, 24(1):85-89, 1988.

Sinnett et al., "Fast Integrated Flow Plethysmograph for Small Mammals," *J Appl Physiol*, 50(5):1104-1110, 1981.

Sales Brochure, Harvard Apparatus, "Double-Chamber Plethysmographs," www.harvardapparatus,com, 1 page (retrieved on Nov. 24, 2006).

ACOUSTIC PLETHYSMOGRAPH FOR MEASURING PULMONARY FUNCTION

CROSS-REFERENCE TO RELATED APPLICATION

This application claims the benefit of U.S. Provisional Application No. 60/958,537, filed Jul. 6, 2007, which is incorporated herein by reference.

ACKNOWLEDGMENT OF GOVERNMENT SUPPORT

This invention was made by the National Institute for Occupational Safety and Health, Centers for Disease Control and Prevention, an agency of the United States Government.

FIELD

The present disclosure concerns embodiments of an acoustic plethysmograph for measuring pulmonary function.

BACKGROUND

Measurement of tidal volume in conscious, unrestrained mice has traditionally been performed using a whole-body plethysmograph (WBP). Such a device includes a chamber in which a mouse is placed. Pressure changes in the chamber due to respiration are observed, which are then related to tidal volume. The advantages of this type of system over a restrained plethysmograph are the extreme ease of use, reduced stress on the animal, and the ability for repeated and prolonged measurements.

Drorbaugh and Fenn related tidal volume to the pressure changes measured in a closed chamber due to thermo-hygrometric differences between respired air and gas within the chamber. (Drorbaugh, J. E. and W. O. Fenn. A barometric method for measuring ventilation in newborn infants. *Pediatrics*, 16:81-87, 1955.) Epstein and Epstein later pointed out a systematic error when only inspiratory events are used to calculate tidal volume. (Epstein, M. A. and R. A. Epstein. A theoretical analysis of the barometric method for measurements of tidal volume. *Respir Physiol*, 32:105-120, 1978.) Epstein et al., later proposed a method to account for these systematic errors. (Epstein, R. A., M. A. Epstein, G. G. Haddad, and R. B. Mellins. Practical implementation of the barometric method for measurement of tidal volume. *J Appl Physiol*, 49:1107-15, 1980.) At nearly the same time, Jacky also proposed an improved method of analysis that permitted long term measurements of tidal volume. (Jacky, J. P. Barometric measurement of tidal volumes: effects of pattern and nasal temperature. *J Appl Physiol*, 49:319-325, 1980.) All barometric plethysmograph techniques assume that changes in plethysmograph pressure can be accounted for solely by changes in temperature and humidity.

It is known, however, that gas compression in the lung can also contribute significantly to the pressure measured in an unrestrained plethysmograph. Frazer et al., demonstrated the effects of compression on the WBP signal with a model validated by simultaneously measuring plethysmograph pressure and chest wall motion of guinea pigs with a laser displacement sensor. (Frazer et al. Estimation of guinea pig airway resistance following exposure to cotton dust measured with a whole body plethysmograph. In: Proceedings of the Twenty-First Cotton and Organic Dust Research Conference, edited by R. R. Jacobs and P. J. Wakelyn, vol. 12, pp. 171-174. 1997.) Enhorning et al., used a mechanical model of the chest to show that plethysmographic pressure was not only affected by breathing pattern, but also by airway resistance. (Enhorning et al. Whole-body plethymography, does it measure tidal volume in small animals? *Can J Physiol Pharmacol*, 76:945-951, 1989.) Although there is some controversy as to the extent and conditions under which gas compression becomes a significant portion of the WBP signal measured in mice, it is clear that tidal volume measurements of mice with increased airway resistance or breathing rate are likely to contain a significant component related to gas compression.

Further, previous attempts to measure specific airway resistance with a conventional WBP have failed largely because changes in these measurements can be explained not only by changes in airway resistance, but also by changes in the tidal volume breathing pattern. Lundblad et al., showed that gas compression could be estimated by conditioning the chamber air to near alveolar conditions, but that estimates of airway resistance still require knowledge of the tidal breathing pattern. (Lundblad, L. K. A., C. G. Irvin, A. Adler, and J. H. T. Bates. A reevaluation of the validity of unrestrained plethysmography in mice. *J Appl Physiol*, 93:1198-1207, 2002.)

SUMMARY

The present disclosure concerns embodiments of an acoustic plethysmograph for measuring pulmonary function of an animal, such as a mouse. The plethysmograph in exemplary embodiments can measure thoracic tidal volume of an unrestrained animal; that is, an animal that is retained in a chamber of the plethysmograph without a seal around the animal's head or neck to separate the thoracic and nasal flow of the animal. Thoracic tidal volume can be used with the traditional plethysmograph measurement (box flow) to provide an input-output model of the animal's respiratory system based on a single chamber plethysmograph, much like researchers have done in the past using a double chamber plethysmograph containing a restrained animal. Such model can then be used to determine the specific airway resistance of the animal.

The plethysmograph in some embodiments acoustically excites the chamber containing the animal and detects changes in the acoustic pressure in the chamber. These acoustic pressure changes correlate with the changes in animal volume, referred to as the volume breathing pattern or thoracic tidal volume. Thoracic tidal volume is equal to the sum of tidal volume (airway tidal volume) and lung gas compression volume. Because lung gas compression volume is very small compared to thoracic tidal volume, thoracic tidal volume provides a close approximation of tidal volume. In contrast, the lung gas compression volume can become a very significant portion of the measurement using a conventional whole-body plethysmograph. The acoustic plethysmograph therefore can provide a more accurate measurement of tidal volume as compared to a conventional whole-body plethysmograph.

The plethysmograph also can be configured to measure chamber flow (the flow of air into and out of the chamber), such as with a flow meter positioned to measure airflow through a nozzle of the chamber or a pressure transducer or gauge that can measure the measure drop of the airflow through the nozzle, which can be correlated to airflow through the nozzle. Specific airway resistance of the animal can be determined from the thoracic tidal volume and plethysmograph flow measurements. For example, the plethysmograph flow signal can be integrated to determine chamber volume (the volume of the air flow into and out of the plethysmograph chamber). The transfer function from thoracic tidal volume to chamber volume can then be determined. The specific airway resistance of the mouse can then be determined from the transfer function. Because thoracic tidal volume is measured directly, specific airway resistance can be assessed more accurately than traditional techniques utilizing the whole-body plethysmograph which must assume thoracic tidal volume is constant.

In particular embodiments, the plethysmograph includes a moveable wall that is configured to adjust the volume of the plethysmograph chamber, and therefore the dead space volume of the chamber (the volume in the chamber surrounding the animal). This allows the dead space volume in the acoustically excited chamber to be adjusted to a value such that changes in the dead space volume caused by respiration of the animal produce substantially linear changes in the acoustic pressure in the chamber. Inspiration corresponds to a decrease in acoustic pressure while expiration corresponds to an increase in acoustic pressure. A microphone or equivalent mechanism can be used to detect the acoustic pressure changes. A processor can be used to determine the thoracic tidal volume of the animal based on the pressure changes.

In a representative embodiment, an apparatus for measuring pulmonary function of an animal comprises an enclosure adapted to enclose the animal, a signal generator operable to generate an acoustic signal that is transmitted through the enclosure, a signal detector operable to detect the acoustic pressure inside the enclosure, and a processor operable to determine the thoracic tidal volume of the animal based on a change in acoustic pressure inside the enclosure.

In another representative embodiment, an apparatus for measuring pulmonary function of an animal comprises an enclosure defining a chamber and adapted to receive the entire body of an unrestrained animal in the chamber and a device operable to measure thoracic tidal volume of the animal in the chamber based on changes in acoustic pressure in the chamber.

In another representative embodiment, an apparatus for measuring pulmonary function of an animal comprises an enclosure defining a chamber and adapted to receive the entire body of an unrestrained animal in the chamber. The apparatus further includes means for measuring thoracic tidal volume of the animal in the chamber, means for measuring gas flow into and out of the chamber, and means for determining a value representative of the animal's airway resistance based on the gas flow into and out of the chamber and the thoracic tidal volume of the animal.

In yet another representative embodiment, a method for measuring pulmonary function of an unrestrained animal is provided. The method comprises placing the unrestrained animal in a chamber and determining a thoracic flow signal of the animal in the chamber based on changes in the acoustic pressure in the chamber.

In another representative embodiment, a method for measuring pulmonary function of an animal inside a chamber comprises generating an acoustic signal that is transmitted through the chamber, measuring a change in acoustic pressure inside the chamber caused by a change in the volume of the animal's body, and determining the thoracic tidal volume of the animal from the change in acoustic pressure.

In still another representative embodiment, an apparatus for measuring pulmonary function of an animal comprises an enclosure defining a chamber and adapted to receive the entire body of an unrestrained animal in the chamber. The enclosure comprises a nozzle having an opening and a moveable wall that is moveable to adjust the volume of the chamber and therefore the dead space volume surrounding the animal. The apparatus also can include a signal generator operable to generate an acoustic signal that is transmitted through the enclosure, a signal detector operable to detect the acoustic pressure inside the enclosure, an airflow-measuring device operable to measure airflow through the nozzle, and a processor operable to determine the thoracic tidal volume of the animal based on a change in acoustic pressure inside the enclosure and to determine a value representative of the animal's airway resistance based on the thoracic tidal volume and the airflow through the nozzle.

The foregoing and other features and advantages of the invention will become more apparent from the following detailed description, which proceeds with reference to the accompanying figures.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

First Representative Embodiment

Figures 1, 2:
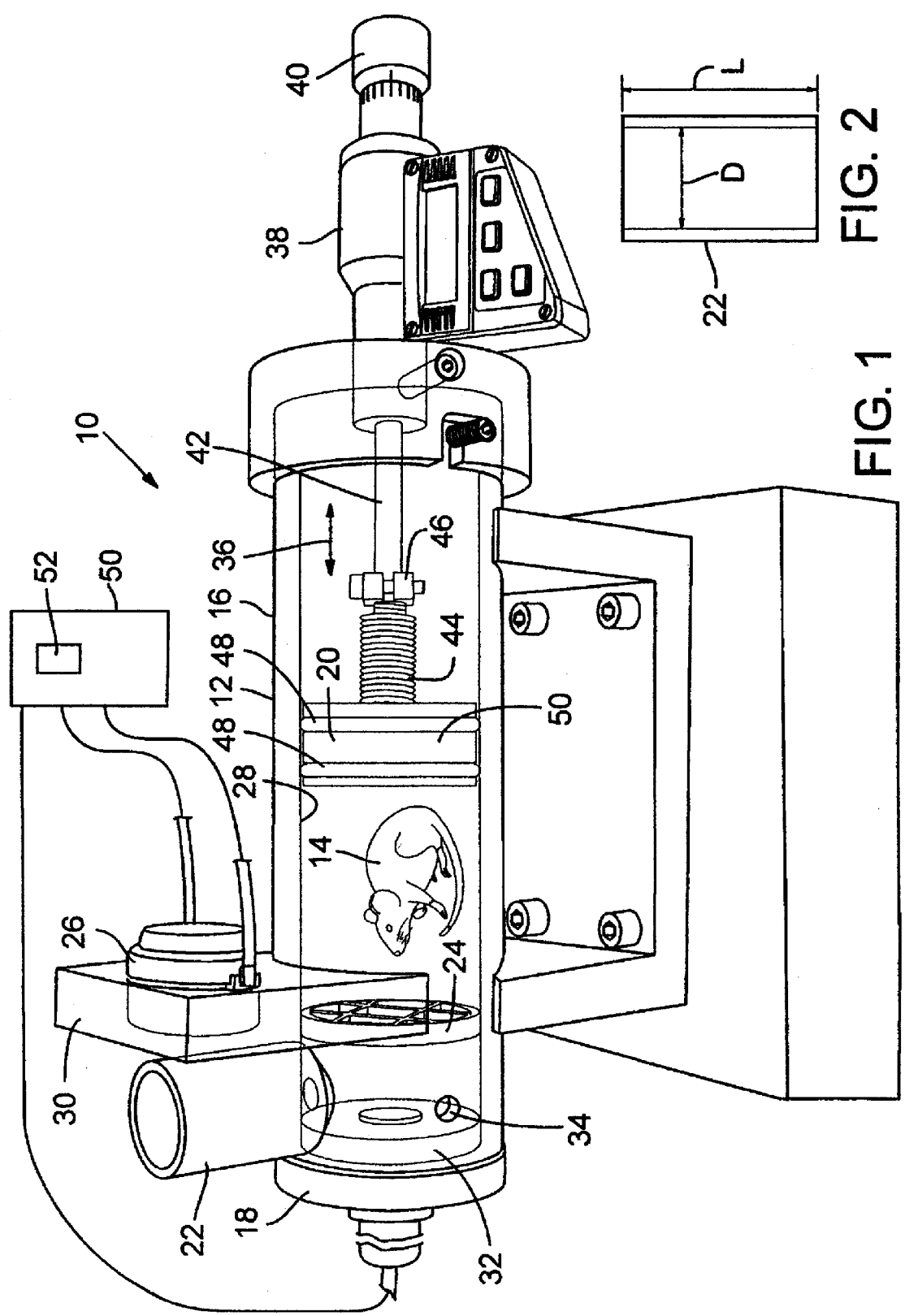
FIG. 1 is a perspective view of a disclosed embodiment of a whole-body plethysmograph for measuring pulmonary function of an animal.
FIG. 2 is a side view of the nozzle of the plethysmograph shown in FIG. 1.

FIG. 1 shows an exemplary embodiment of a plethysmograph 10 for measuring pulmonary function of an animal. The illustrated embodiment is adapted for use with a small animal, such as a mouse or guinea pig. In other implementations, however, the apparatus can be adapted for use with larger animals, such as dogs or humans. The plethysmograph 10 includes an enclosure, or housing, 12 defining a chamber 28 for receiving the entire body of an unrestrained animal, such as the illustrated mouse 14. In the context of the present disclosure, a chamber that receives the entire body of an unrestrained animal means that the chamber does not include a seal around the animal's head or neck to separate the thoracic and nasal flow of the animal.

The enclosure 12 in the illustrated embodiment includes an elongated cylindrical or tubular body 16 defining the side wall of the enclosure, a first end wall 18 closing one end of the tubular body 16, a second, moveable end wall, or stop, 20, and an open neck portion, or nozzle, 22 adjacent the first end wall 18. The nozzle 22 is in communication with the chamber 28 via an opening in the body 16. The opening in the illustrated embodiment desirably has a diameter equal to the inner diameter D of the nozzle 22 (FIG. 2). A restraining member 24, such as an apertured plate or a mesh screen, desirably is positioned in the chamber to restrain the mouse 14 in the space behind the nozzle 22 so that the mouse does occlude the nozzle.

An acoustic signal generator, or speaker, 26 is provided to generate an acoustic signal that is transmitted through the chamber. The speaker 26 can be mounted to the top of the enclosure 12 adjacent the nozzle 22, such as via the illustrated bracket 30 mounted adjacent the nozzle. The bracket 30 can be formed with an opening for receiving and the supporting the speaker 26 as shown. The speaker 26 alternatively can be positioned at any convenient location that allows signals generated by the speaker to acoustically excite the chamber. The speaker 26 in certain embodiments is operable to generate a sinusoidal output signal.

An acoustic signal detector 32, such as the illustrated microphone, is positioned to detect the acoustic pressure inside the chamber 28. The microphone 32 can be mounted in an opening in the end wall 18 as shown. A small flow port 34 can be provided in the enclosure 12 to introduce a bias flow of air to flush out carbon dioxide and to keep the mouse cool. The port 34 can be used to fluidly connect the chamber to a pressure transducer for measuring the pressure drop of the airflow through the nozzle 22, as shown in the embodiment shown in FIG. 9 and described below. The dimensions of the flow port 34 and any tubing or fluid conduit extending therefrom (e.g., conduit connecting the port 34 to a pressure transducer) are selected such that the impedance of the port and any tubing has little or no effect on the resonance of the enclosure 12.

The end wall 20 is configured to be moveable longitudinally (lengthwise) of the enclosure 12 (in the directions indicated by double-headed arrow 36) to vary the volume of the chamber 28, and therefore the dead space volume in the chamber (the volume of the chamber less the volume of the animal's body), the significance of which is described in detail below. A micrometer 38 or equivalent mechanism can be used to move the end wall 20 a desired distance in either direction to increase or decrease the volume of the chamber 28.

In the illustrated embodiment, the micrometer 38 has an adjustment knob 40 and a rotatable shaft 42 that is operable to extend and retract (in the directions indicated by double-headed arrow 36) to adjust the overall length of the micrometer by rotation of the adjustment knob. The shaft 42 desirably is fixedly secured to one end of a threaded shaft 44 such as by a clamp mechanism 46. The opposite end of the threaded shaft 44 extends into and is connected to a ball joint in the end wall 20 such that rotational and longitudinal movement of the shaft 44 causes corresponding longitudinal movement of the end wall 20 without rotational movement of the end wall. Thus, rotation of the knob 40 causes the end wall 20 to move longitudinally inside the chamber to increase or decrease the volume of the chamber. The end wall 20 can carry one or more o-rings 48 seated in annular grooves formed in the annular outer surface 50 of the end wall 20 to form a substantially air-tight seal between the end wall 20 and the adjacent inner surface of the tubular body 16.

Alternative techniques or mechanisms can be used to produce movement of the end wall 20 within the tubular body. For example, an electric motor, such as a stepper motor, can be operatively connected to the end wall to produce movement thereof. Additionally, in some embodiments, and unlike the micrometer 38, the adjustment mechanism used to move the end wall 20 need not be capable of measuring linear movement of the end wall. Additionally, other sealing mechanisms can be used in lieu of or in addition to the o-rings 48 to form a substantially air-tight seal between the end wall 20 and the inner surface of the body 16.

The plethysmograph 10 can have a controller, or processor, 50 that can be operatively connected to the speaker 26 and the microphone 32. The controller 50 is operable to receive output signals from the microphone 32 and determine a thoracic flow signal representative of the tidal volume of the mouse 14 based on changes in the acoustic pressure inside the chamber 28. The controller 50 can also be operable to control the output of the speaker 26. The controller 50 can have a memory for recording data, such as tidal volume, and a visual display 52 for displaying tidal volume and other physiological characteristics of the mouse detected by the plethysmograph. The controller 50 can be, for example, a general purpose computer.

Figure 3:
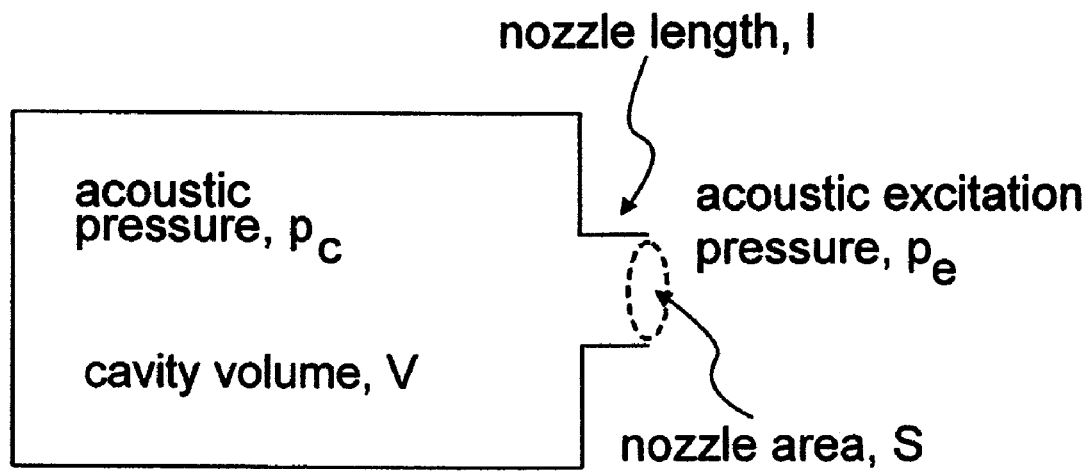
FIG. 3 is a schematic side view of a Helmholtz resonator.

Explaining now the operation of the plethysmograph 10, the plethysmograph operates as a resonant cavity, or a Helmholtz resonator consisting of a cavity with an open neck, or nozzle, such as schematically show in FIG. 3. This system has an acoustic resonance at a frequency determined by the nozzle dimensions and the cavity (chamber) volume. When considering acoustic wavelengths much larger than cavity dimensions, a sinusoidal source with amplitude $p_e$ transmitted through the cavity will produce a pressure signal amplitude inside the cavity given by:

$$p_c = \frac{p_e}{[(1-\omega^2/\omega_0^2)^2 + \omega^2 R^2 C^2]^{\frac{1}{2}}} \quad (1)$$

where $\omega$ is the excitation frequency, $\omega_0$ is the resonant frequency, R is the acoustic resistance of the nozzle, and C is the compliance of the air in the chamber. Both $\omega_0$ and C are dependent on the volume, V, of the cavity and can be described by the following equations:

$$\omega_0 = \sqrt{\frac{c_0^2 S}{lV}}, \quad (2)$$

$$C = \frac{V}{\rho_0 c_0^2}. \quad (3)$$

Figure 4:
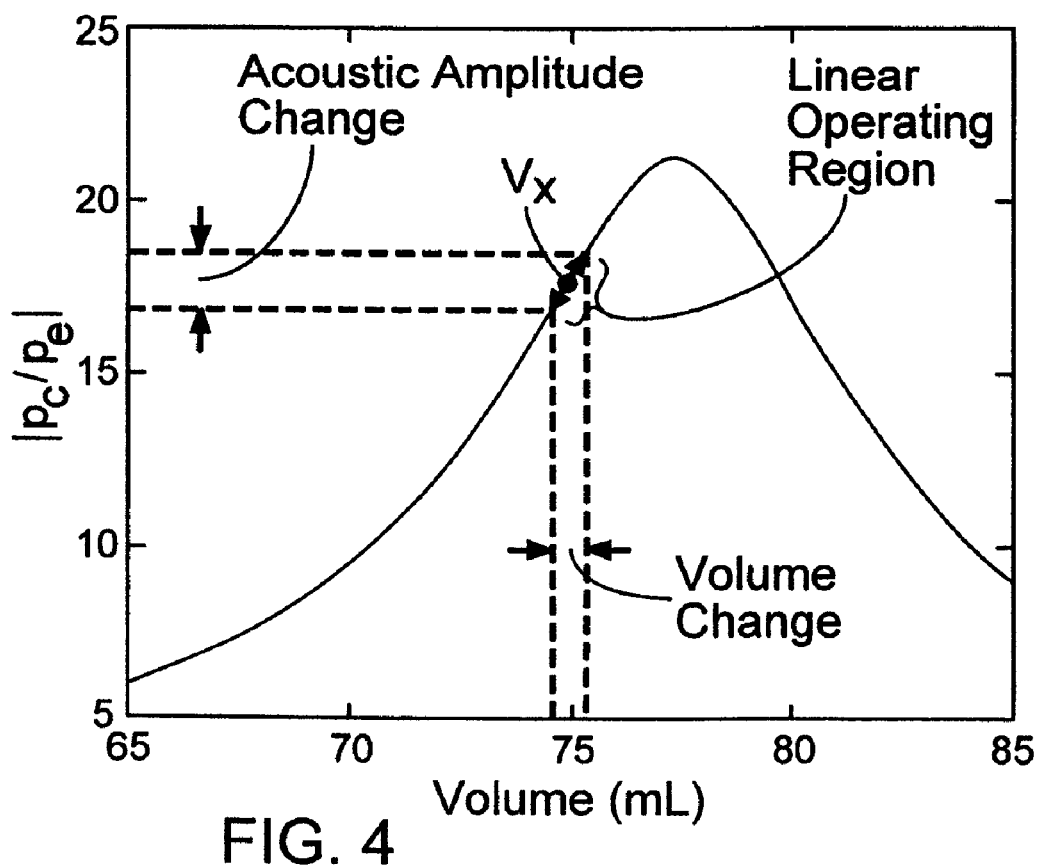
FIG. 4 is a graph of the ratio of excitation pressure to chamber acoustic pressure versus cavity volume of a whole-body plethysmograph.

In these expressions, $c_0$ is the speed of sound, S is the nozzle cross sectional area, l is the effective length of the nozzle, and $\rho_0$ is the density of air. Given the nozzle dimensions l and S and the resistance R, the chamber volume at which the peak pressure amplitude $p_c$ occurs can be determined. FIG. 4, for example, shows the magnitude of the ratio $p_c/p_e$ versus volume for a chamber with nozzle dimensions l=4 cm, S=0.785 cm$^2$, and a resistance of R=0.0004 cmH$_2$0 sec cm$^{-3}$. The peak output of the ratio $p_c/p_e$ in this example occurs at a cavity volume of approximately 77 mL. As shown in FIG. 4, to the left of the peak, there is a region on the curve that is nearly linear. The midpoint of this region is denoted $V_x$ on the graph, and represents the operating point of the plethysmograph. When the acoustic excitation ($p_e$) is held at a constant frequency and amplitude, small perturbations about $V_x$ will produce substantially linear changes in the output acoustic pressure amplitude ($p_c$).

In use, a mouse 14 (or another animal species) is placed in the chamber 28, as depicted in FIG. 1, and the chamber dead space volume is adjusted to a value within the range of $V_x$. As described above, the dead space volume can be adjusted by turning the adjustment knob 40 of the micrometer 38, which in turn causes the end wall 20 to move in the desired direction. After setting the dead space volume, the chamber is acoustically excited by the speaker 26, which produces an acoustic signal with an excitation pressure $p_e$. As the mouse respires and its chestwall expands and contracts, the dead space volume changes, which modulates the amplitude of the acoustic pressure $p_c$ in the chamber. Because the acoustic input impedance of the mouse respiratory system, beginning with the large change in area from the chamber to the nasal opening, is very large, the volume of air inside the lungs has little or no effect on the acoustic pressure in the plethysmograph chamber 28. Inspiration corresponds to a decrease in output amplitude while expiration corresponds to an increase in output amplitude. The microphone 32 detects the acoustic pressure in the chamber and provides an output signal to the processor 50, which are proportional to the thoracic tidal volume of the mouse 14.

When used with mice, the speaker 26 can be used to generate an acoustic signal having a frequency in the range of about 250 Hz to about 350 Hz, with a frequency of about 300 Hz being a specific example. However, frequencies outside of this range can be used depending on the size of the animal and the geometry of the chamber 28. The higher the sound pressure level (SPL) inside the chamber relative to undesirable environmental noise near the excitation frequency, the better the signal to noise ratio. For this reason, the sensitivity of the system increases with an increase of the SPL. Because the hearing range of mice does not extend below 2000 Hz, a higher SPL can be tolerated than has been used in systems designed for humans.

As noted above, the traditional WBP (whole body plethysmograph) has been used to measure tidal volume assuming the pressure signal results solely from thermo-hygrometric differences between respired and ambient air. Although the effects of gas compression on the WBP signal of normal mice may be negligible, gas compression in mice with an altered breathing pattern and/or increased airway resistance can produce significant errors in the measurement of tidal volume using a conventional WBP. For example, the slope of the rising edge of an individual breath can increase even when the breathing rate goes down. Therefore, lung gas compression can increase due to an increase in frequency content even when breathing rate is reduced. An advantage of the acoustic plethysmograph 10 in exemplary embodiments is the ability to measure the tidal volume of an animal independent of gas compression. This is particularly useful when monitoring animals with increased gas compression, such as caused by the exposure to a respiratory irritant or toxin that increases either airway resistance or the frequency content of the breathing pattern.

Example 1

A plethysmograph 10 was constructed from a plexiglass tube with a 3.68 cm internal diameter. A microphone 32 was mounted in a fixed plate which sealed one end of the chamber. A micrometer 38 comprised a model 762 electronic micrometer head (The L.S. Starrett Company, Athol, Mass.). The micrometer was used to adjust the chamber volume, which could be varied from approximately 60 to 120 mL.

The nozzle 22 had a length L (FIG. 2) of about 3.5 cm and an internal diameter D (FIG. 2) of about 1.1 cm. The speaker 26 was driven by a model 220 function generator (Medi Cal Instruments, Inc., Lewis Center, Ohio) to generate a sine wave output. Acoustic pressure inside the chamber was measured with a model 2530 microphone, a model 910B pre-amp, and a model 2200C power supply (Larson Davis, Depew, N.Y.). The plethysmograph was shielded from noise from the surrounding environment by placing it in a box lined with acoustic foam. Band pass filtering the output signal prior to demodulation also can be used to reduce the effects of external noise and noise generated by the animal. All data was digitized at a rate of 10 kHz with a 16-bit data acquisition board and custom program (National Instruments, Model 6063E and LabView) after passing through a 1-kHz anti-aliasing filter (National Instruments, Model SC-2345 and SCC-LP04).

Signal processing in this example was performed using Matlab (The Mathworks Inc., Natick, Mass.). The plethysmograph was designed to be excited by a single frequency ($f_o$) constant amplitude sine wave. The acoustic pressure signal measured inside the chamber 28 was first passed through a band pass filter with corner frequencies at $f_o-15$ Hz and $f_o+15$ Hz. The amplitude was demodulated by calculating the magnitude of the Hilbert transform. This signal was then related to thoracic tidal volume using the calibration technique described below.

The excitation frequency of the plethysmograph was selected by setting the chamber volume to 75 mL. The frequency of the function generator was adjusted in the 250 to 350 Hz range until the maximum output signal was obtained. Next, a mouse was placed in the chamber 28, which decreased the plethysmograph dead space. The output signal varied as the animal's volume changed during respiration. The DC component of this signal represents the output at the average dead space volume. The plethysmograph volume was adjusted until the DC output was maximized. This represents the peak output amplitude at this excitation frequency and chamber dead space volume. The plethysmograph volume was then decreased by 2 mL in order to move from the peak of the output curve to a point in the linear operating region (i.e., $V_x$ in FIG. 4). This designates the operating point of the plethysmograph. The excitation amplitude was then adjusted until the mean sound pressure level (SPL) in the chamber was 110 dB. A three point calibration was obtained by measuring the DC voltage output at three volumes: at the operating point, at the operating point minus 400 µL, and at the operating point plus 400 µL. These calibration volumes were achieved by adjusting the micrometer 34. The slope of the best-fit straight line of the calibration data is the ratio of voltage to volume.

The accuracy of the plethysmograph was tested by measuring the change in volume of a water-filled balloon inside the chamber connected to an external syringe pump. A 250-µL syringe was incorporated in the pump and connected to the balloon through the plethysmograph bias flow port 34. The initial balloon volume was approximately 20 mL, representing the volume of a typical mouse. All connections were made with stiff-walled Teflon tubing. A three-way valve was connected inline for initial filling of the balloon and purging of air from the system. A linear potentiometer attached to the syringe pump was used to record syringe displacement. The system was calibrated as described above. The syringe pump was programmed to move between 0 and 250 µL at a maximum rate of about 527 µL/min. Because the syringe pump produced a slight vibration, the data for this test were post-processed with a 30-msec moving average filter.

A step test also was used to assess the response time of the system. Since the syringe pump was not fast enough for this purpose, the step test was administered manually. The syringe assembly was disengaged from the screw drive and the test was performed by manually pushing the syringe assembly as fast as possible.

Figure 5:
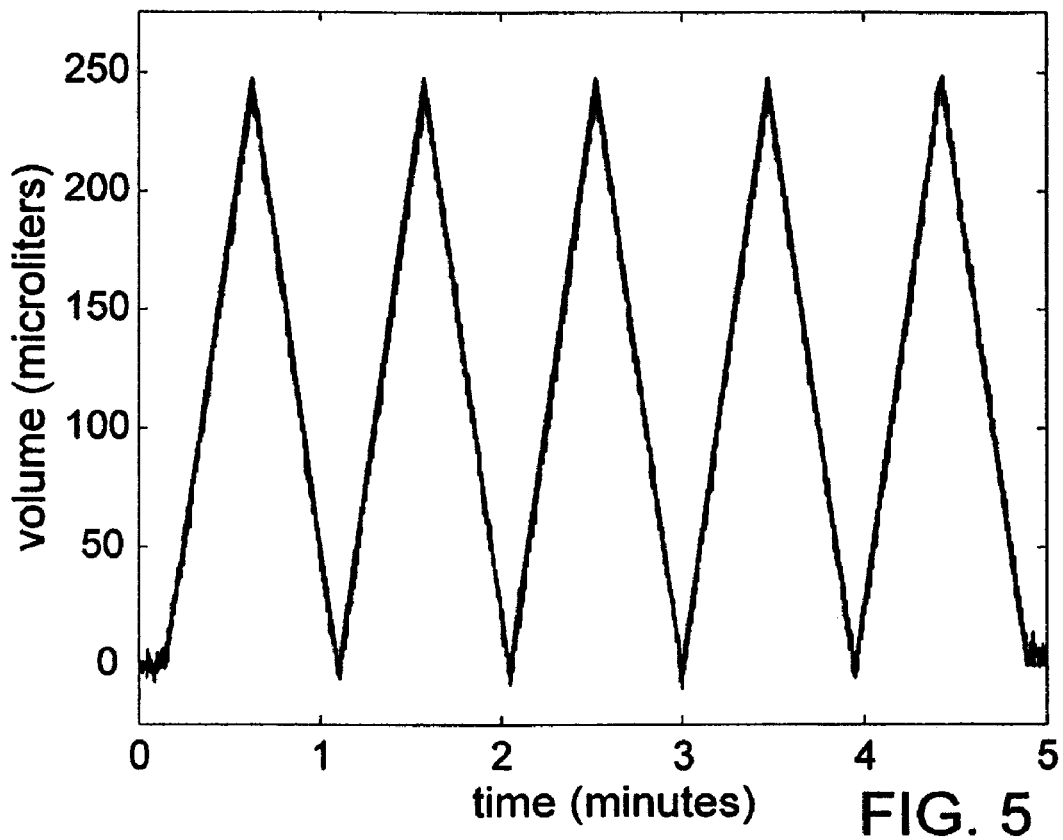
FIG. 5 is a graph of syringe pump volume and plethysmograph output volume versus time demonstrating the response time of a whole-body plethysmograph.
Figure 6:
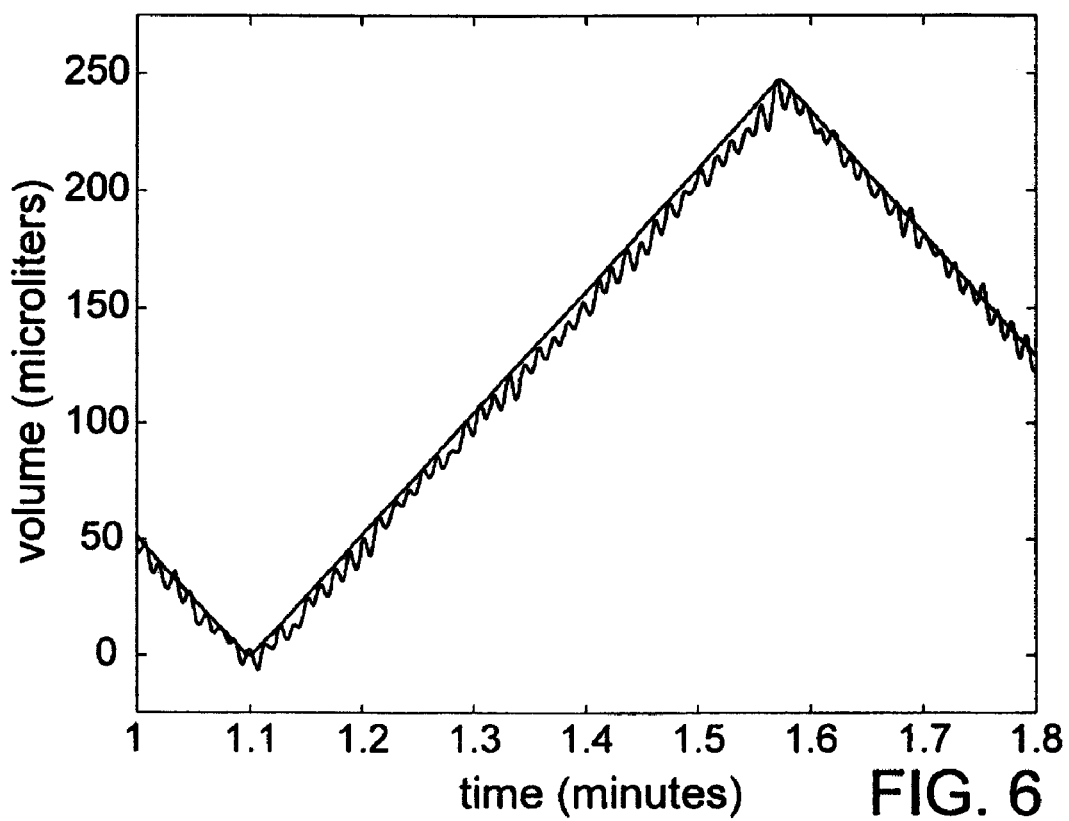
FIG. 6 is an enlarged view of a portion of the graph shown in FIG. 5.
Figure 7:
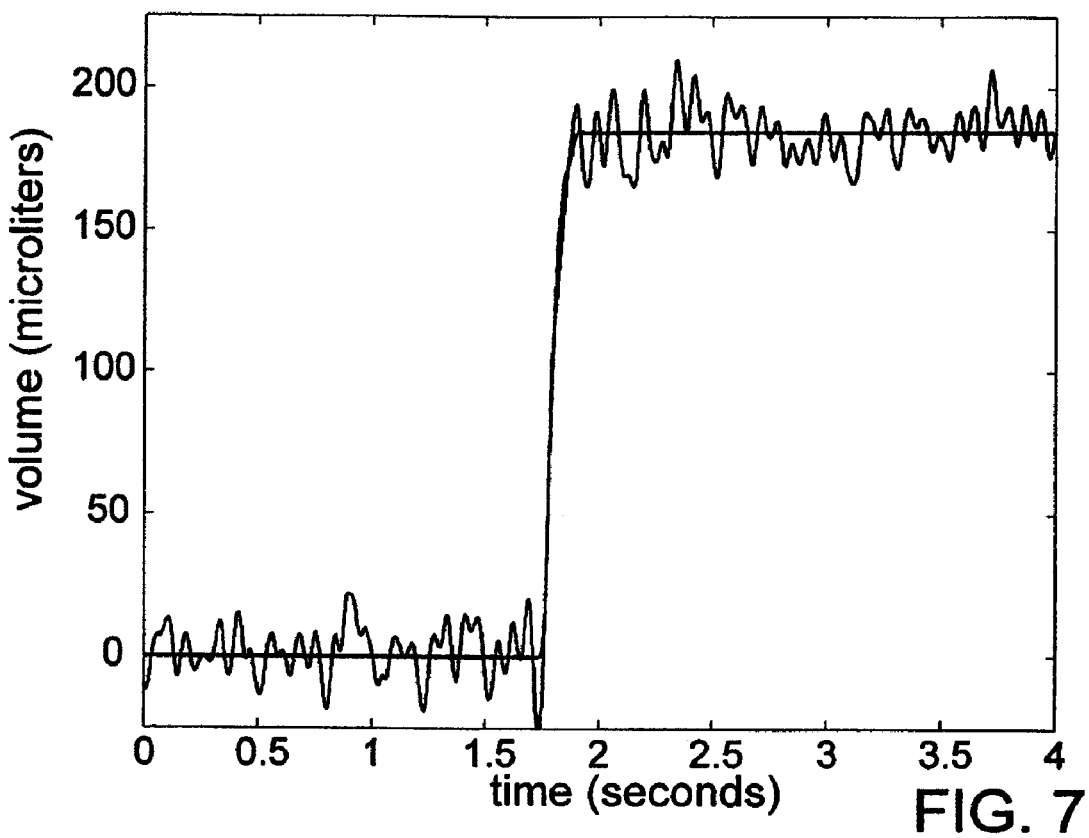
FIG. 7 is a graph of syringe pump volume and plethysmograph output volume versus time demonstrating the response time of a whole-body plethysmograph.

Results of the water-filled balloon test are shown in FIGS. 5 and 6. Specifically, FIG. 5 shows the volume change of the balloon measured by the plethysmograph over time. Since it is difficult to see the syringe volume signal in FIG. 5, a zoomed view of a portion of the graph is shown in FIG. 6. The root-mean-square error over the five minute test was 4.43 µL. The standard deviation of the error was 4.09 µL. The results of the step test is shown in FIG. 7. Since the syringe step was generated manually, the final volume of the step was less than 250 µL. This was to avoid the noise generated by banging the end of the syringe. Also, the displacement of the syringe is not a true step. However, the results of this example demonstrate that the plethysmograph is able to track extremely fast changes in volume. The time for the input to increase from 10% to 90% of the peak value was 7.91 msec. The 10% to 90% rise time of the output was 8.83 msec, resulting in a difference of less than 1 msec.

Figure 8:
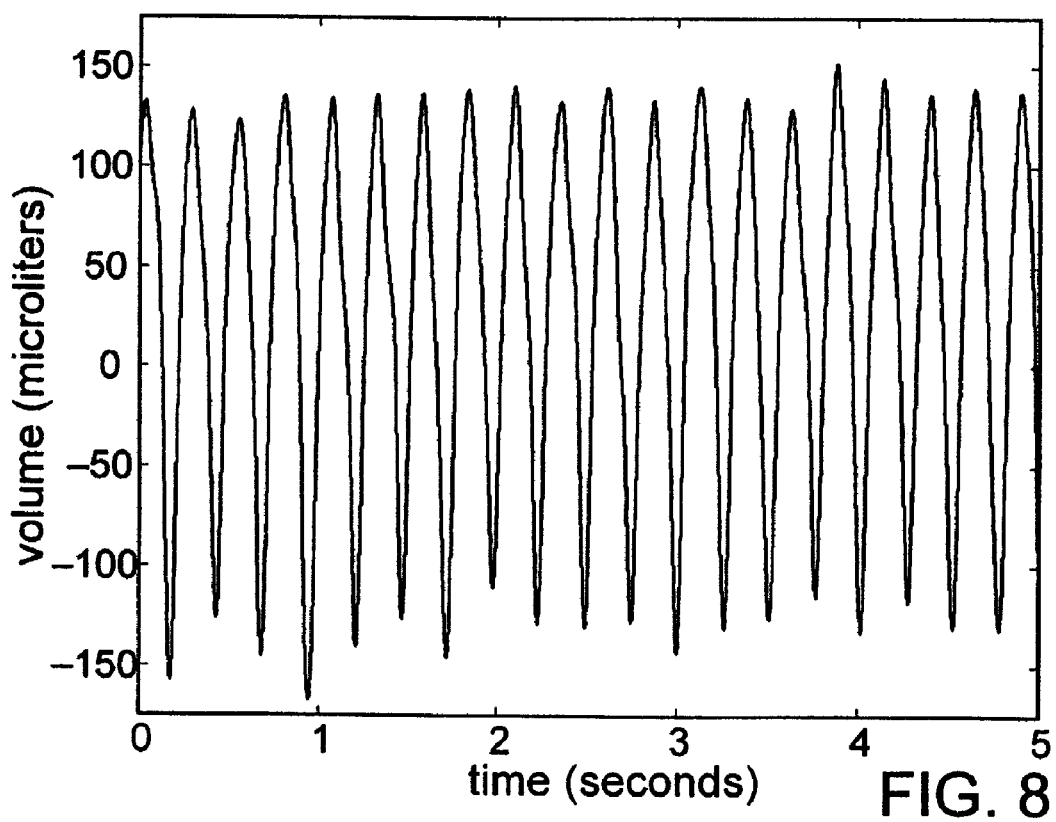
FIG. 8 is a graph of thoracic tidal volume of a mouse versus time measured using a whole-body plethysmograph.

Finally, the plethysmograph was used to measure the thoracic tidal volume of a 19-gram specific pathogen-free female A/J mouse (Jackson Laboratory). The animal was housed in an AAALAC-accredited animal facility at 23 deg C. and 50% humidity with a 12-hour light/dark cycle, and was provided standard laboratory mouse chow and tap water ad libitum. The mouse was weighed and placed in the chamber, and thoracic tidal volume measured. FIG. 8 displays the plethysmograph output (thoracic tidal volume) for the A/J mouse. The average peak-to-peak thoracic tidal volume of each breath (±standard deviation) was 270 µL (±15.8 µL). The average rate of breathing (±standard deviation) was 3.95 Hz (±0.196 Hz).

Second Representative Embodiment

Figure 9:
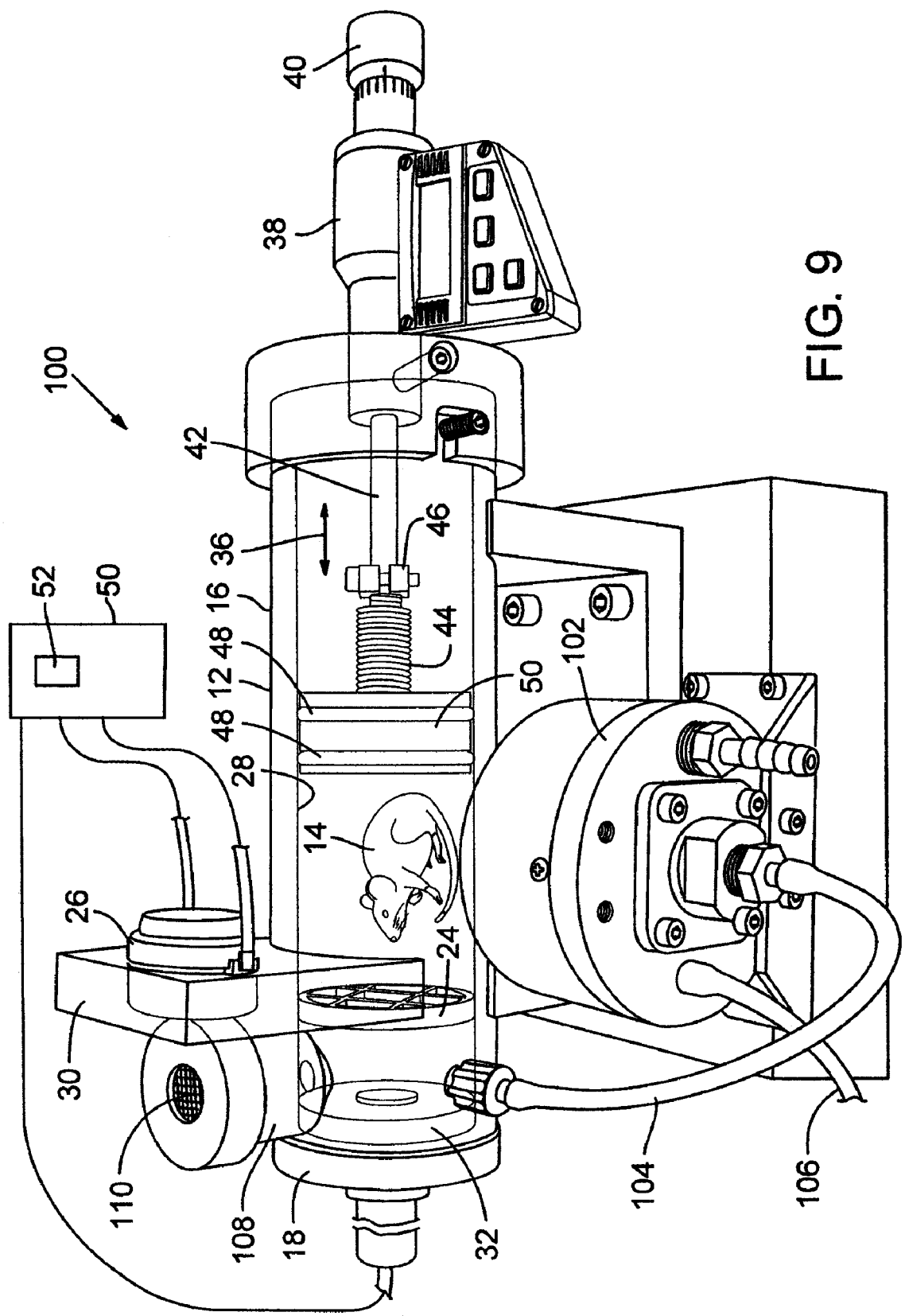
FIG. 9 is a perspective view of another exemplary embodiment of a whole-body plethysmograph for measuring pulmonary function of an animal.

FIG. 9 shows another embodiment of a plethysmograph, indicated generally at 100. This embodiment shares many similarities with the embodiment of FIG. 1. Hence, components in FIG. 9 that are identical to corresponding components in FIG. 1 have the same respective reference numerals and are not described further. The plethysmograph 100 in this embodiment includes a pressure transducer 102 operable to measure the pressure of the atmosphere in the chamber 28 relative to barometric pressure. One end of a flexible tube 104 opens into the chamber 28 at opening 34. The opposite end of the tube 104 is connected to the pressure transducer 102. The pressure transducer 102 can be operatively connected to a controller 50, such as via a lead 106.

The plethysmograph 100 in the illustrated embodiment also includes a nozzle 108 that includes a mesh screen 110 that extends across the nozzle opening. In use, the pressure transducer 102 measures the pressure drop across the screen 110, which is proportional to air flow into and out of the chamber 28. As air flows through the nozzle 108, the pressure transducer provides output signals to the controller 50, which determines air flow into and out of the chamber based on the pressure drop across the screen 110. Thus, the plethysmograph 100 in the illustrated embodiment can be used to measure a thoracic tidal volume signal of an animal as well as a plethysmograph flow signal (representative of airflow through the nozzle). By measuring both signals, a value representative of airway resistance can be determined. For example, the flow signal can be integrated to determine chamber volume (the volume of the air flow into and out of the plethysmograph chamber). The transfer function from thoracic tidal volume to chamber volume can then be determined. The specific airway resistance of the mouse can then be determined from the transfer function.

In an alternative embodiment, a flow meter, such as an ultrasonic flow meter, can be used to measure airflow through the nozzle 108 rather than the pressure transducer 102. If a flow meter is used, the screen 110 would not be needed. Removing the screen can reduce the resistance of the system, which in turn increases the volume sensitivity. Advantageously, an increase in volume sensitivity can facilitate calibration and reduce noise degradation of volume measurement.

Model of Respiratory System

Figure 10A:
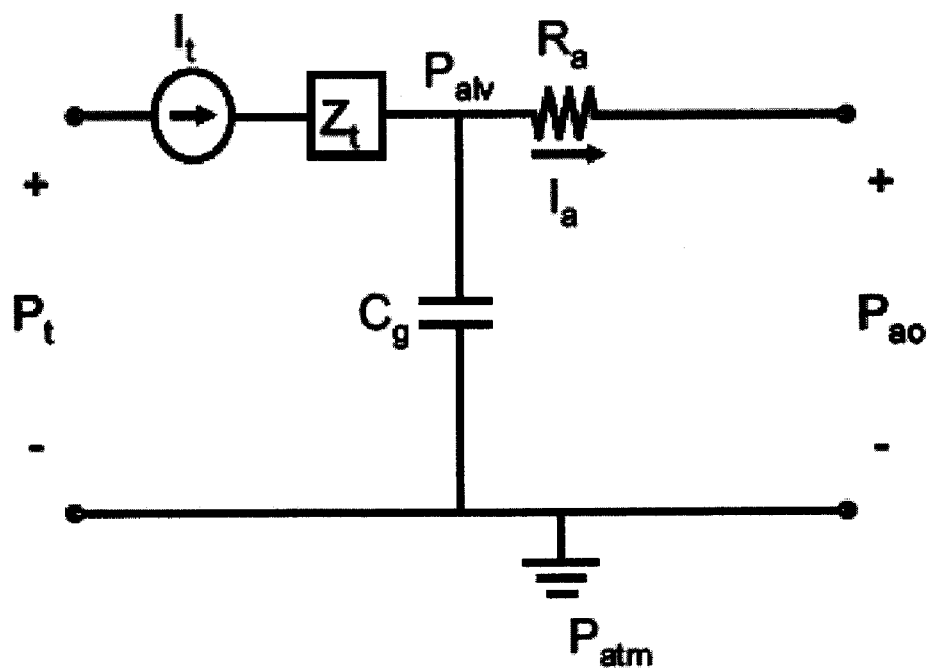
FIG. 10A is an electric circuit representation of a respiratory system.
Figure 10B:
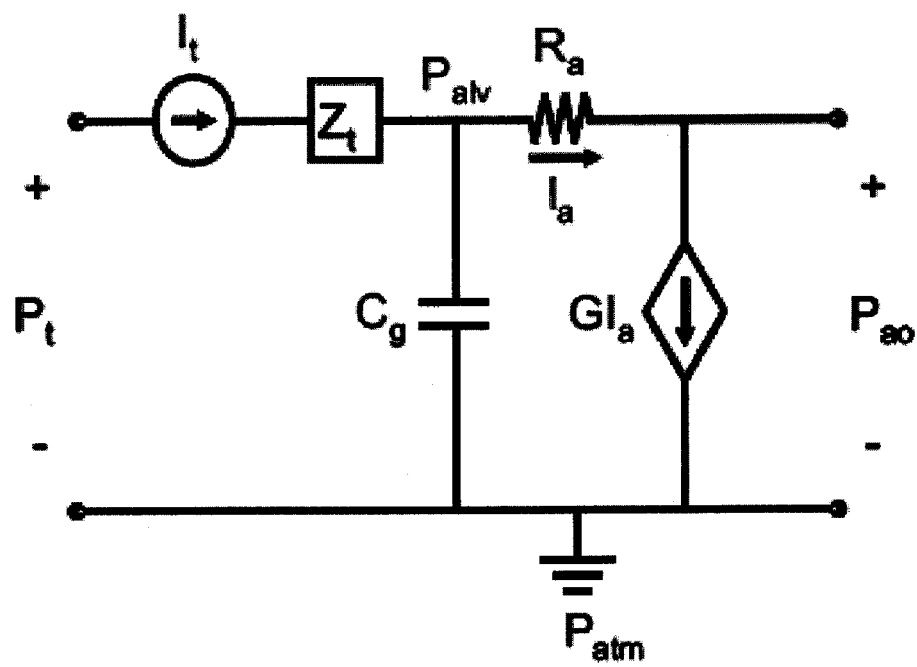
FIG. 10B is an electric circuit representation of a respiratory system incorporating the gain G on airway flow due to changes in temperature and humidity.

Specific airway resistance can be derived from a model of the respiratory system as shown in FIG. 10A. (Pennock B E, Cox C P, Rogers R M, Cain W A, and Wells J H. A noninvasive technique for measurement of changes in specific airway resistance. *J Appl Physiol.* 46(2):399-406, 1979). The current source, $I_t$, represents the thoracic flow produced by the animal. $Z_t$ represents the impedance of the lung tissues, $I_a$, represents flow in the airways, $R_a$ represents the flow resistance of the airways, and $C_g$ represents the compressibility of the gas in the lung and airways. $P_t$ and $P_{ao}$ represent the pressures (relative to atmospheric pressure) produced at the thorax and airway opening, respectively. $P_{alv}$ is alveolar pressure and $P_{atm}$ is atmospheric pressure. Note that the direction of the currents indicated in FIGS. 10A-10D are for expiration and are reversed during inspiration.

When an animal respires air at room conditions the gas is warmed and humidified on inspiration and the reverse (approximately) takes place on expiration. Therefore, there is an effective change in volume flow due to this thermo-hygrometric effect. This thermo-hygrometric "flow" ($I_{th}$) is in phase with $I_a$ and can be modeled as:

$$I_{th} = G I_a. \quad (4)$$

The dependent voltage source, $GI_a$, represents the steady state fraction of volumetric flow lost from the change in temperature and humidity between alveolar and box conditions. The value of G, the gain on airway flow, is:

$$G = \left[1 - \frac{T_c(P_a - P_{H_2Oa})}{T_a(P_c - P_{H_2Oc})}\right] \quad (5)$$

where the subscripts c and a denote conditions of inspired and alveolar gas, respectively, and T and P are temperature and pressure, respectively. Incorporating this effect results in the model shown in FIG. 10B. (Drorbaugh, J E and Fenn W O. A barometric method for measuring ventilation in new-born infants. *Pediatrics,* 16:81-87, 1955).

It has been suggested that the differences between inspiratory and expiratory conditions would necessitate separate calculations of G. (Epstein et al., A theoretical analysis of the barometric method for measurement of tidal volume, *Respir Physiol,* 32:105-120, 1978). Consider an animal placed inside a whole-body plethysmograph. During inspiration, the gas is warmed from chamber temperature to body temperature and humidified from chamber humidity to saturation. In humans, expiratory gas exits at nasal conditions of approximately 32 degrees C. and saturated with water vapor. Id. While the human respiratory tract is not a very efficient heat exchanger, that of a small rodent is much more efficient. Schmid studied the exit temperature of respired air for many small mammals, including several species of mouse, and found that the exit temperature to be approximately 1 degree C. above ambient. (Schmid W D, Temperature gradients in the nasal passage of some small mammals, *Comp Biochem Physiol,* 54A:304-308, 1975).

Consider a mouse inspiring air at 50% relative humidity and 22 degree C., with expiratory conditions of 100% relative humidity and 23 degrees C. For this case, the inspiratory value of G is 0.0956 and the expiratory value is 0.0816, a difference of approximately 17%. For an animal placed in a chamber with an open nozzle, the relative humidity in the chamber will increase with each breath until the moisture added per breath is equal to the moisture leaving the chamber via diffusion. Therefore, the inspiratory G will move toward the expiratory G the longer the animal stays in the chamber. As such, there is a slight variation in G from inspiration to expiration during tidal breathing. Also, small baseline changes in G might occur if the efficiency of heating and cooling is affected by changes in respiratory rate, depth of breathing, core temperature, etc. The model used here considers a fixed G estimated as the average of the inspiratory G calculated at room conditions and the expiratory G calculated at 100% relative humidity and 1 degree C. above room temperature. Room temperature and relative humidity as used herein are 22.7 degrees C. and 47%, respectively. Using an assumed body temperature of 37 degrees C. resulted in an average G of 0.084.

Figure 10C:
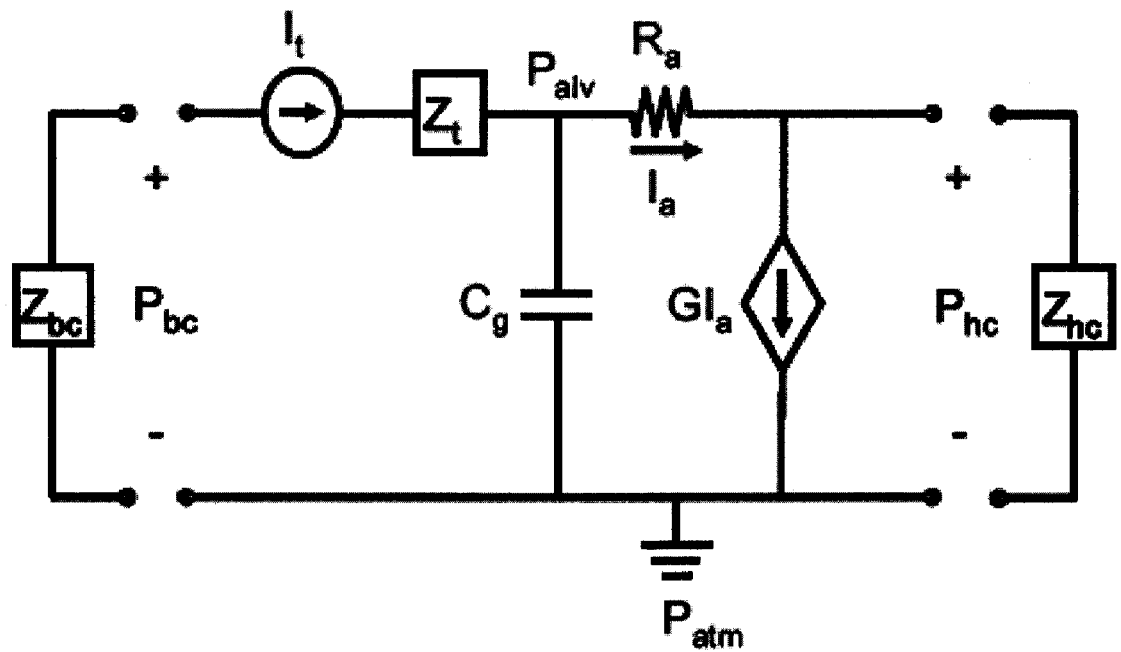
FIG. 10C is an electric circuit representation of a restrained animal in double-chamber plethysmograph.
Figure 10D:
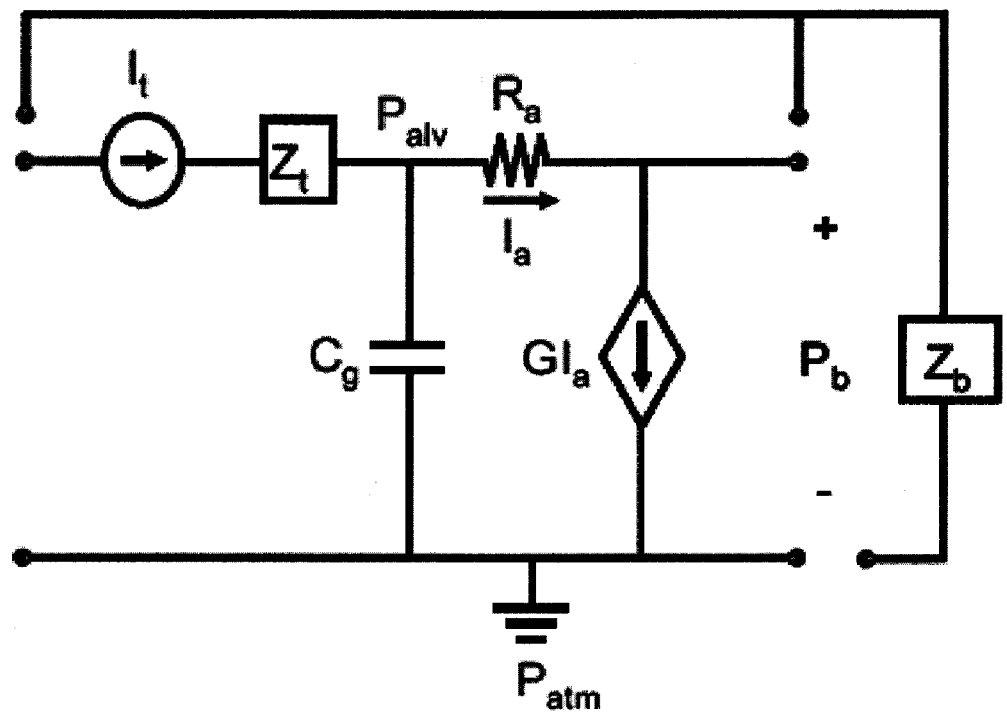
FIG. 10D is an electrical circuit representation of an unrestrained animal in a whole-body plethysmograph.
Figure 11:
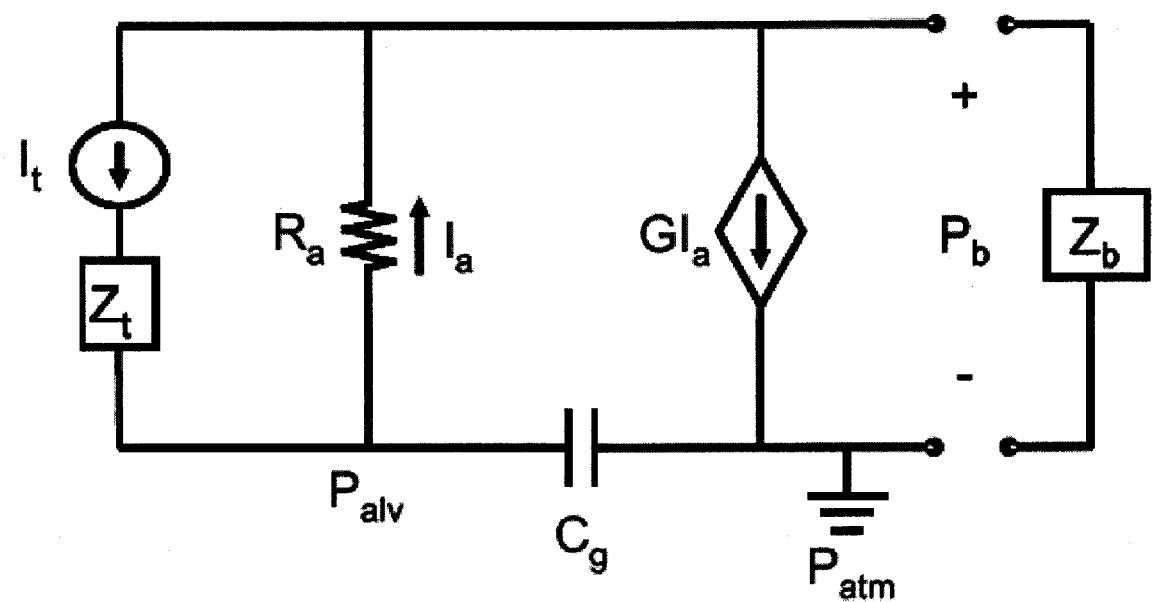
FIG. 11 shows the circuit of FIG. 10D redrawn in a more concise manner.

Now consider an animal placed in a double-chamber plethysmograph (DCP) which is the traditional system used to estimate sRaw. The conventional DCP uses a neck seal to enable simultaneous measurement of nasal flow and thoracic flow. FIG. 10C shows the electric analogue corresponding to the DCP. Here, $Z_{bc}$ represents the impedance of the body chamber and $Z_{hc}$ represents the impedance of the head chamber. This system restrains the animal, but allows independent measurements of two flows (or pressures) from which sRaw can be estimated. When animal is placed in an unrestrained whole-body plethysmograph (WBP) as disclosed herein, there is an interaction between the thorax and nasal flows (i.e., no neck seal). FIG. 10D shows an electric circuit analogue corresponding to the unrestrained WBP. Here, $Z_b$ represents the box impedance. Without modification, this circuit can be redrawn as shown in FIG. 11. This represents the low-frequency bulk flow model of the unrestrained WBP.

An expression for specific airway resistance can be derived based on the model shown in FIG. 11. Summing the currents in the lung yields:

$$I_a(t) + I_c(t) - I_t(t) = 0 \quad (6)$$

where $I_c(t)$ is the current into the capacitor, Cg:

$$I_c(t) = C_g \frac{dP_{alv}(t)}{dt}. \quad (7)$$

Alveolar pressure is given by the equation:

$$P_{alv}(t) = R_a I_a(t) + P_b(t) \approx R_a I_a. \quad (8)$$

Since the box pressure is extremely small compared to alveolar pressure, the box pressure term can be neglected. Substitutions into the preceding equation gives:

$$I_c(t) = R_a C_g \frac{dI_a(t)}{dt} \quad (9)$$

Now, substituting this expression into Equation 6 and solving for thoracic flow:

$$I_t(t) = I_a(t) + R_a C_g \frac{dI_a(t)}{dt}. \quad (10)$$

Summing the currents at the airway opening yields:

$$I_b(t) + I_a(t) - G I_a(t) - I_t(t) = 0. \quad (11)$$

Solving for airway flow provides:

$$I_a(t) = \frac{I_t(t) - I_b(t)}{1 - G}. \quad (12)$$

Substitution into Equation 10 and rearranging gives:

$$I_b(t) + R_a C_g \frac{dI_b(t)}{dt} = G I_t(t) + R_a C_g \frac{dI_t(t)}{dt}. \quad (13)$$

Taking the Laplace transform:

$$I_b(s) + R_a C_g I_b(s)s = G I_t(s) + R_a C_g I_t(s)s \quad (14)$$

$$I_b(s)(1 + R_a C_g s) = I_t(s)(G + R_a C_g s) \quad (15)$$

The transfer function from thoracic flow to box flow is:

$$\frac{I_b(s)}{I_t(s)} = \frac{G + R_a C_g s}{1 + R_a C_g s}. \quad (16)$$

Then the transfer function from thoracic volume, $V_t$, to box volume, $V_b$, is equal to the transfer function from thoracic flow to box flow Let box volume be the integral of box flow:

$$\frac{I_b(s)}{I_t(s)} = \frac{s \cdot V_b(s)}{s \cdot V_t(s)} = \frac{V_b(s)}{V_t(s)} = \frac{G + R_a C_g s}{1 + R_a C_g s}. \quad (17)$$

Since the derivative is inherently noisy, it is more convenient to integrate box flow and use volume signals than to take the derivative of thoracic volume and use flow signals.
Substituting $s = j\omega$:

$$\frac{V_b(j\omega)}{V_m(j\omega)} = \frac{G + j\omega R_a C_g}{1 + j\omega R_a C_g}, \quad (18)$$

$$\frac{V_b(j\omega)}{V_t(j\omega)} = \frac{G + j\omega R_a C_g}{1 + j\omega R_a C_g} \cdot \frac{1 - j\omega R_a C_g}{1 - j\omega R_a C_g}, \quad (19)$$

$$\frac{V_b(j\omega)}{V_t(j\omega)} = \frac{G + \omega^2 R_a^2 C_g^2 + j(1-G)\omega R_a C_g}{1 + \omega^2 R_a^2 C_g^2} \quad (20)$$

The phase angle, $\theta$, between thoracic volume and box volume therefore is given by:

$$\tan\theta = \frac{(1-G)\omega R_a C_g}{G + \omega^2 R_a^2 C_g^2} \quad (21)$$

Rearranging:

$$\omega^2 \tan\theta (R_a C_g)^2 - \omega(1-G) R_a C_g + G \tan\theta = 0. \quad (22)$$

Solving for $R_a C_g$:

$$R_a C_g = \frac{(1-G) \pm \sqrt{(1-G)^2 - 4G\tan^2\theta}}{2\omega\tan\theta}. \quad (23)$$

Only the smaller root of the above equation yields physiologically relevant values (see discussion below):

$$R_a C_g = \frac{(1-G) - \sqrt{(1-G)^2 - 4G\tan^2\theta}}{2\omega\tan\theta}. \quad (24)$$

Alternately, dropping the higher order term of Equation 22 provides reasonable accuracy. This results in the following solution:

$$R_a C_g \equiv \frac{G\tan\theta}{2\pi(1-G)f}. \quad (25)$$

Figure 13:
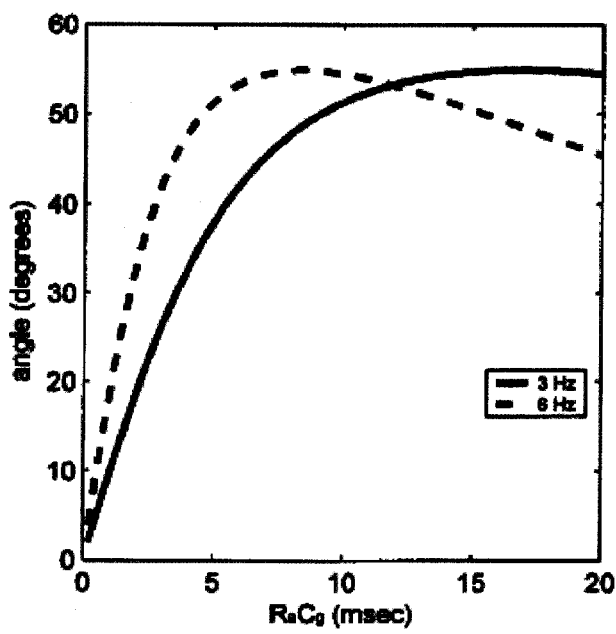
FIG. 13 shows curves representing theoretical phase response, as a function of $R_a C_g$, of the model shown in FIG. 11 at 3 Hz and 6 Hz.

In order to infer specific airway resistance from the phase shift of the transfer function given in Equation 20, Equation 22 must be solved for $R_a C_g$. Since Equation 22 is quadratic in $R_a C_g$, the phase angle, $\theta$, initially increases with an increase in $R_a C_g$, but eventually reaches a peak and then decreases as $R_a C_g$ continues to increase. As a result, there are two solutions for any given phase shift. FIG. 13 displays the phase angle versus airway resistance-compliance for the model at two frequencies and G=0.1. A reasonable approach is to use only the portion of the curve that is monotonically increasing (that is, the smaller of the two solutions).

Figure 14:
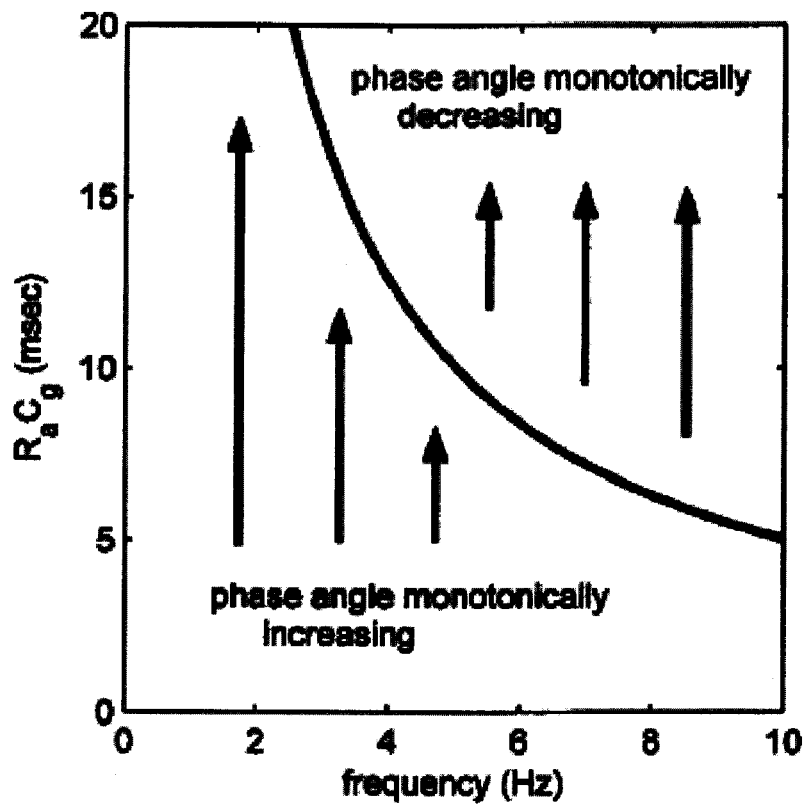
FIG. 14 is a curve showing the peak phase angle as a function of frequency and $R_a C_g$ of the model.

It can be shown that the value of the peak angle is constant for a constant G. However, the phase angle reaches a peak at a lower $R_a C_g$ as frequency increases. The curve denoting the peak angle (which is constant for constant G) as a function of frequency and $R_a C_g$ is shown in FIG. 14. Given the breathing frequency, this curve defines the maximum $R_a C_g$ that can be inferred from the phase angle. As an example, consider a mouse breathing at 5 Hz. As the animal's airways constrict, the phase angle would increase until $R_a C_g$ reaches approximately 10 msec. As the airways continue to narrow, the phase would begin to drop, appearing as though $R_a C_g$ were actually decreasing. However, since the $R_a C_g$ for normal mice is approximately 1 msec, it would appear to be an extreme case for $R_a C_g$ to cross the limit shown in FIG. 14. Even for a mouse breathing at the unusually high frequency of 10 Hz, airway resistance-compliance could quintuple before the limit would be reached.

Figure 15:
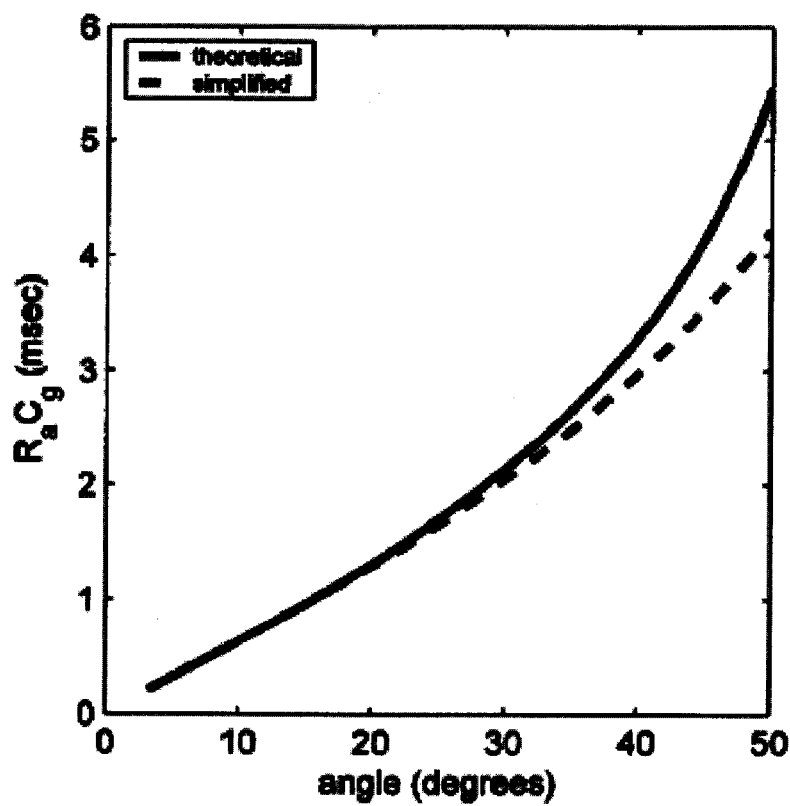
FIG. 15 displays $R_a C_g$ as a function of phase angle for Equations 24 and 25.

Finally, for f=5 Hz, FIG. 15 displays $R_a C_g$ as a function of the phase angle for Equations 24 and 25. The simplified expression of Equation 25 produces a slight underestimation of $R_a C_g$. For assessing mice whose $R_a C_g$ is in the range of normal to 300% of normal, Equation 25 provides reasonable accuracy.

Specific Airway Resistance
Specific airway resistance is defined as:

$$s_{Raw} \equiv R_a \cdot TGV \quad (26)$$

where TGV is thoracic gas volume. Gas compliance in the lung (assuming isothermal conditions) can be written as:

$$C_g \equiv \frac{TGV}{P_{atm} - P_{H2Oa}}. \quad (27)$$

By substituting Equation 27 into Equation 26, it is seen that specific airway resistance is equal to the time constant $R_a C_g$ multiplied by pressure $P_{atm} - P_{H2Oa}$:

$$s_{Raw} = R_a \cdot C_g \cdot [P_{atm} - P_{H2Oa}]. \quad (28)$$

In particular embodiments, measurements are made over a relatively short span of time. Therefore, the pressure term can be considered a constant, and $R_a C_g$ is then a direct measure of specific airway resistance. In the present disclosure, estimates of $R_a C_g$ have units given in milliseconds. However, if sRaw is estimated based on $P_{atm} - P_{H2Oa} \cong 1000$ cm $H_2O$, then from Equation 28:

$$sRaw = R_a C_g \text{ m sec} \cdot 1000 \text{ cm } H_2O \quad (29)$$

$$= 1000 \cdot R_a C_g \text{ cm } H_2O \cdot \text{msec} \quad (30)$$

$$= R_a C_g \text{ cm } H_2O \cdot \text{sec}. \quad (31)$$

Under these conditions, sRaw in units of cm $H_2O \cdot$sec will have the same numerical value as $R_a C_g$ in units of msec.

Hence, specific airway resistance of an unrestrained animal can be determined by applying the above equations. In one specific approach, specific airway resistance can be calculated by first measuring thoracic tidal volume of the animal in the chamber 28 and chamber flow, and then integrating chamber flow to determine chamber volume. The angle of the transfer function from thoracic tidal volume to chamber volume can be determined, which can then be used to determine the specific airway resistance $R_aC_g$ using Equation 24 or Equation 25. In another approach, specific airway resistance can be calculated by measuring thoracic tidal volume and chamber flow and then taking the derivative of the thoracic tidal volume to determine thoracic flow. Thereafter, the transfer function from thoracic flow to chamber flow can be determined, which can be used to calculate specific airway resistance.

While in the embodiment described above the phase of the transfer function is used to calculate specific airway resistance, this is not a requirement. In alternative embodiments, specific airway resistance can be calculated from the phase angle and/or the magnitude of the transfer function, or from the time domain relationship between thoracic tidal volume and chamber volume. In addition, FIG. 11 provides one example of a model that can be used to represent the respiratory system of an animal. Other models, which can be more sophisticated than the one shown in FIG. 11, also can be used. Further, in some cases, the transfer impedance of the animal's respiratory system can be used without any particular model to screen/evaluate changes in lung function.

Example 2

Six A/J mice (18.5 to 23.0 g) were exposed to aerosolized saline and three doses of the broncho-constrictive agent methacholine chloride dissolved in saline (5 mg/mL, 10 mg/mL, and 20 mg/mL doses). For each dose, the mice were placed in a traditional whole-body plethysmograph (WBP) where they were exposed for two minutes to measure Penh. Three minutes after exposure, the mice were moved to an acoustic plethysmograph 100 where box (chamber) flow and thoracic tidal volume were measured for two minutes at a sampling rate of 1000 Hz. Since all six mice were tested at each concentration prior to increasing to the next concentration of methacholine, the time between doses for each mouse was approximately 45 minutes. All animal procedures were performed in accordance with an animal protocol approved by the NIOSH institutional animal care and use committee.

The pressure drop across the screen 110 was measured with a model 239 differential pressure transducer available from Setra Systems, Inc. The speaker 26 produced a constant frequency acoustic signal at about 300 Hz.

Although the acoustic plethysmograph is designed to be a second-order system having a resonant frequency near 300 Hz, Sinnett, et al. (Sinnett et al. Fast integrated flow plethysmograph for small mammals, *J Appl Physiol,* 50(5):1104-1110, 1981) show that these types of flow plethysmographs act as first-order systems at low frequencies. Furthermore, they show that a flow plethysmograph with a first-order time constant of 1.5 msec or less has a fast enough response for accurate measurement of forced vital capacity maneuvers in mice. Given the acoustic plethysmograph volume (about 75 mL) and screen resistance (0.00224 cm $H_2O \cdot sec \cdot mL^{-1}$), the first-order time constant is approximately 0.168 msec in isothermal conditions and 0.120 msec in adiabatic conditions. Since flow is inferred from pressure at low frequencies in this example (mouse breathing frequencies (<10 Hz)), whether the system operates in either an adiabatic or isothermal mode (or changes between the two) has little effect on the box flow measurement.

All data (mean±SE) were analyzed using one-way ANOVA followed by post hoc analysis using Fisher's PLSD. Log transformation was applied to equalize variance between doses. Dose-response trends were determined using regression analysis. Differences were considered significant at p<0.05.

The electro-mechanical delay between the pressure transducer and the microphone was assessed by lightly tapping the nozzle opening with no animal in the chamber. This produced a pressure drop across the screen while simultaneously interrupting the acoustic signal measured by the microphone. These data were used to calculate the phase shift produced by the electro-mechanical properties of the transducers, which was subsequently subtracted from the phase shift measured with the animal present in the plethysmograph.

Each signal was filtered with a 15 Hz low-pass filter for noise reduction. Box flow was integrated to determine box volume. The data were broken into six second segments with a 50% overlap. That is, the first segment was from t=0 seconds to t=6 seconds; the second segment from t=3 seconds to t=9 seconds; etc. An estimate of the transfer function was computed using Welch's averaged periodogram method (Matlab "tfe" function) with a 2000-point transform size, a 2000-point window, and an overlap of 1000 samples. Using these same parameters, an estimate of the coherence was determined for each segment.

For each time segment, the angle of the transfer function was determined at the breathing frequency by linear interpolation from the estimate above. This angle and breathing frequency were used with Equation 24 to calculate an estimate of $R_aC_g$ for each segment. Similarly, coherence for each segment was determined at the breathing frequency. The mean $R_aC_g$ value for each mouse was found by averaging the estimates for all the segments whose coherence was greater than or equal to 0.9.

Figure 12A:
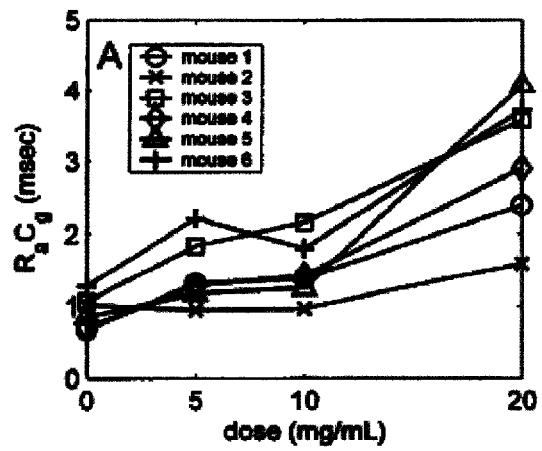
FIG. 12A shows the changes in specific airway resistance of mice in response to different doses of methacholine chloride aerosol in a whole-body plethysmograph.
Figure 12B:
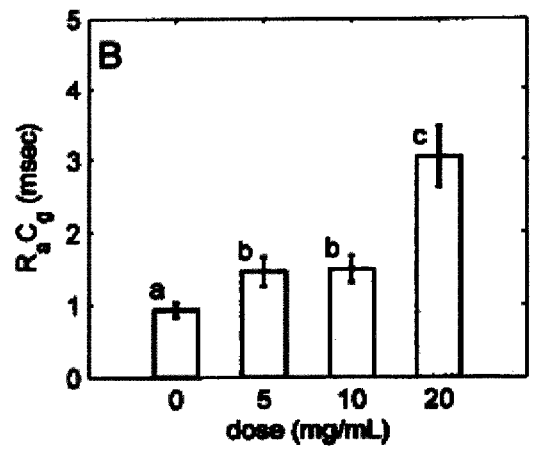
FIG. 12B shows the mean specific airway resistances shown in FIG. 12A at each dose of methacholine chloride.
Figure 12C:
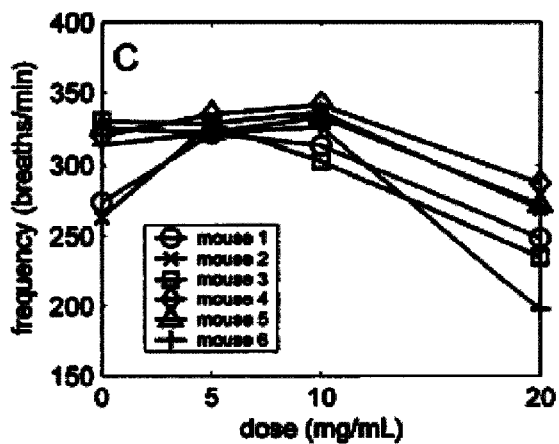
FIG. 12C shows the changes in breathing frequency for each mouse in response to the doses of methacholine chloride.
Figure 12D:
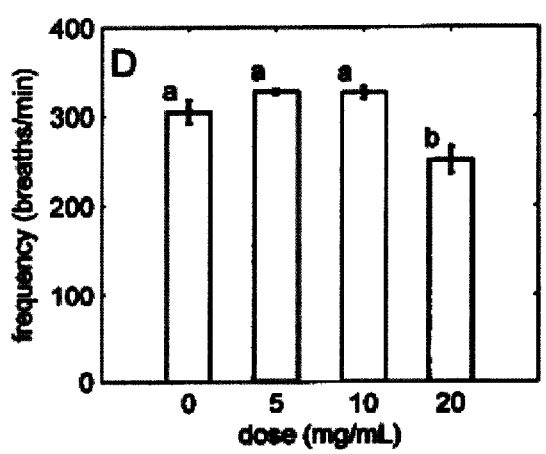
FIG. 12D shows the mean breathing frequency of the mice at each dose of methacholine chloride.
Figure 12E:
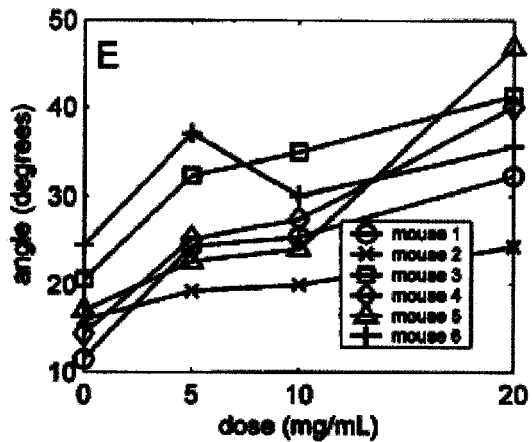
FIG. 12E shows the changes of the phase angle for each mouse in response to the doses of methacholine chloride.
Figure 12F:
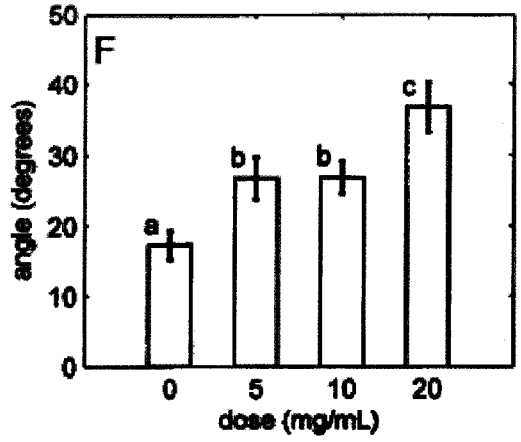
FIG. 12F shows the average phase angle of the mice at each dose of methacholine chloride.

The results of the methacholine aerosol exposure are shown in FIGS. 12A-12F. At the 5 and 10 mg/mL doses, five of the six mice had elevated $R_aC_g$ compared to baseline (FIG. 12A). At the highest methacholine dose (20 mg/mL), each mouse had an increased $R_aC_g$ compared to saline. This mean increase from baseline for 5 to 10 mg/mL doses was 57% and 61%, respectively. At the 20 mg/mL dose, the mean increase was over 227%, or a little more than a tripling of $R_aC_g$.

The airway resistance-compliance values were calculated based on the phase shift and the breathing frequency. The results for these two component measurements are shown FIGS. 12C-12F. In general, there is a dose dependent increase in phase shift, accompanied by a decrease in breathing frequency at the highest dose.

The baseline specific airway resistance value of 0.93±0.10 cm $H_2O \cdot sec$ obtained in this example is consistent with previously reported baseline values in A/J mice. Lofgren et al., found baseline sRaw of 0.676±0.027 cm $H_2O \cdot sec$ in A/J mice using a restrained whole-body plethysmograph. (Lofgren et al., Restrained whole body plethysmography for measure of strain-specific and allergen induced airway responsiveness in conscious mice, *J Appl Physiol,* 101:1495-1505, 2006). However, in a direct comparison of systems using BALB/c mice, they found that sRaw determined in their restrained whole-body plethysmograph was about one third the value they measured using a double-chamber plethysmograph. Delorme and Moss measured sRaw in A/J mice using a double-chamber plethysmograph. (DeLorme et al. Pulmonary function assessment by whole-body plethysmography in restrained versus unrestrained mice. *J Pharmacol Toxicol Methods,* 47:1-10, 2002). In two trials performed a minimum of two days apart, they found values of 1.68±0.06 cm $H_2O \cdot sec$ and 1.49±0.14 cm H$_2$O·sec. Additionally, the baseline results in this example are nearly identical to those of Flandre et al. (Flandre et al., Effect of somatic growth, strain, and sex on double-chamber plethymographic respiratory function values in healthy mice. *J Appl Physiol*, 94:1129-1136, 2003) for BALB/c and C57BL/6 mice measured using a double-chamber plethysmograph.

The approach for determining R$_a$C$_g$ in this example is dependent only on the phase of the transfer function. As described above, using only phase limits the range of measurable R$_a$C$_g$. Nonetheless, the limits R$_a$C$_g$ of using phase are high enough that they are believed to be irrelevant for assessing the pulmonary response of a mouse in most cases. Because in this example R$_a$C$_g$ is dependent only on the phase of the transfer function and magnitude is unimportant, it was not necessary to calibrate the thoracic volume or the box volume signal. Moreover, even in the presence of significant noise on the thoracic volume signal, it was possible to measure the increase in airway resistance due to Methacholine Chloride exposure using only the phase of the transfer function. In other embodiments, however, R$_a$C$_g$ can be determined using magnitude and phase information, which would remove the limitations of using only phase information.

It is useful to consider a whole body plethysmograph as a black box with an input and an output. The input represents the flow produced by the animal's thorax. The output represents the plethysmograph flow that is measured in a traditional unrestrained whole body plethysmograph. The black box represents the filtering properties of the respiratory system and the plethysmograph. Using a traditional whole body plethysmograph, only the output of the system or plethysmograph flow is measured. This is the signal from which Penh is measured. The disadvantage of using Penh is twofold. First, Penh has been shown to correlate with changes in the filter (the filtering properties of the respiratory system and the plethysmograph) for some experimental conditions (e.g., methacholine exposure). But, because Penh is empirically derived, there is no guarantee that Penh will change for other experimental conditions even if the filter does change. Second, the output of the system is affected by the input (thoracic flow) and the filter. Without knowledge of the input, it is not possible to know if changes in Penh are due to changes in the filter or due to changes in the input. In contrast, by measuring both the input and output of the system as described above, specific airway resistance can be assessed independent of changes in the animal's respiratory system, such as changes in the animal's breathing pattern.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus for measuring pulmonary function of an animal, comprising:
   an enclosure adapted to enclose the animal;
   a signal generator operable to generate an acoustic signal that is transmitted through the enclosure;
   a signal detector operable to detect the acoustic pressure inside the enclosure; and
   a processor operable to determine the thoracic tidal volume of the animal based on a change in acoustic pressure inside the enclosure;
   wherein the enclosure comprises a moveable wall that is moveable to adjust the internal volume of the enclosure and therefore the dead space surrounding the animal.

2. The apparatus of claim 1, further comprising a micrometer coupled to the wall and operable to move the wall to adjust the internal volume of the enclosure.

3. The apparatus of claim 1, wherein the acoustic signal has a frequency in the range of about 250 Hz to about 350 Hz.

4. The apparatus of claim 3, wherein the acoustic signal has a frequency of about 300 Hz.

5. An apparatus for measuring pulmonary function of an animal, comprising:
   an enclosure defining a chamber and adapted to receive the entire body of an unrestrained animal in the chamber;
   a device operable to measure thoracic tidal volume of the animal in the chamber based on changes in acoustic pressure in the chamber; and
   a device operable to measure gas flow into and out of the chamber.

6. The apparatus of claim 5, further comprising a processor operable to calculate a value representative of the animal's airway resistance based on the thoracic tidal volume of the animal and the gas flow into and out of the chamber.

7. The apparatus of claim 6, wherein the value is the specific airway resistance of the animal.

8. The apparatus of claim 5, wherein the enclosure has an opening and the device operable to measure gas flow comprises a pressure transducer operable to measure a pressure drop of gas flowing through the opening for determining gas flow based on the measured pressure drop.

9. The apparatus of claim 5, wherein the enclosure has an opening and the device operable to measure gas flow comprises a flow meter positioned to receive gas flowing through the opening.

10. The apparatus of claim 5, wherein the device operable to measure thoracic tidal volume is operable to measure acoustic pressure in the chamber and determine thoracic tidal volume of the animal based on a change in the acoustic pressure in the chamber.

11. The apparatus of claim 10, wherein the device operable to measure thoracic tidal volume comprises:
    a signal generator operable to generate an acoustic signal that is transmitted through the chamber;
    a signal detector operable to detect the acoustic pressure inside the enclosure; and
    a processor operable to determine the thoracic tidal volume of the animal based on a change in the acoustic pressure inside the enclosure.

12. An apparatus for measuring pulmonary function of an animal, comprising:
    an enclosure defining a chamber and adapted to receive the entire body of an unrestrained animal in the chamber;
    means for measuring thoracic tidal volume of the animal in the chamber;
    means for measuring gas flow into and out of the chamber; and
    means for determining a value representative of the animal's airway resistance based on the gas flow into and out of the chamber and the thoracic tidal volume of the animal.

13. The apparatus of claim 12, wherein the means for measuring thoracic tidal volume of the animal in the chamber comprises:
    means for generating an acoustic signal that is transmitted through the enclosure;
    means for detecting the acoustic pressure inside the enclosure; and means for determining the thoracic tidal volume of the animal based on a change in the acoustic pressure inside the enclosure.

14. The apparatus of claim 12, further comprising means for adjusting the dead space volume surrounding the animal in the chamber.

15. A method for measuring pulmonary function of an unrestrained animal, the method comprising:
placing the unrestrained animal in a chamber;
determining a thoracic flow signal of the animal in the chamber based on changes in the acoustic pressure in the chamber; and
determining a value representative of the animal's airway resistance based on the thoracic flow signal, wherein determining a value representative of the animal's airway resistance comprises determining a gas flow signal representative of the flow of gas into and out of the chamber and determining a value representative of the animal's airway resistance based on the thoracic flow signal and the gas flow signal.

16. The method of claim 15, wherein determining a value representative of the animal's airway resistance comprises determining the specific airway resistance of the animal based on the thoracic flow signal.

17. The method of claim 16, wherein determining a thoracic flow signal of the animal in the chamber comprises acoustically exciting the chamber, measuring changes in the acoustic pressure in the chamber, and determining the thoracic flow signal based on the changes in the acoustic pressure.

18. A method for measuring pulmonary function of an unrestrained animal, the method comprising:
placing the unrestrained animal in a chamber;
determining a thoracic flow signal of the animal in the chamber based on changes in the acoustic pressure in the chamber; and
wherein prior to determining a thoracic flow signal of the animal in the chamber, the dead space volume surrounding the animal in the chamber is adjusted.

19. A method for measuring pulmonary function of an animal inside a chamber, the method comprising:
generating an acoustic signal that is transmitted through the chamber;
measuring a change in acoustic pressure inside the chamber caused by a change in the volume of the animal's body; and
determining the thoracic tidal volume of the animal from the change in acoustic pressure.

20. The method of claim 19, further comprising calibrating the chamber by adjusting the volume of the chamber until a peak acoustic pressure inside the chamber is achieved and subsequently decreasing the volume of the chamber such that the acoustic pressure inside the chamber is less than the peak acoustic pressure.

21. The method of claim 19, wherein the thoracic tidal volume is determined at a fixed frequency of the acoustic signal.

22. The method of claim 19, further comprising determining the flow rate of gas into and out of the chamber and determining a value representative of the animal's airway resistance based on the thoracic tidal volume and the flow rate of gas into and out of the chamber.

23. An apparatus for measuring pulmonary function of an animal, comprising:
an enclosure defining a chamber and adapted to receive the entire body of an unrestrained animal in the chamber, the enclosure comprising a nozzle having an opening and a moveable wall that is moveable to adjust the volume of the chamber and therefore the dead space volume surrounding the animal;
a signal generator operable to generate an acoustic signal that is transmitted through the enclosure;
a signal detector operable to detect the acoustic pressure inside the enclosure;
an airflow-measuring device operable to measure airflow through the nozzle; and
a processor operable to determine the thoracic tidal volume of the animal based on a change in acoustic pressure inside the enclosure and to determine a value representative of the animal's airway resistance based on the thoracic tidal volume and the airflow through the nozzle.

* * * * *